United States Patent
Hernandez-Garcia et al.

(10) Patent No.: US 10,407,469 B2
(45) Date of Patent: Sep. 10, 2019

(54) PROGRAMMABLE POLYPEPTIDE AND NUCLEIC ACID NANOPARTICLES

(71) Applicant: Northwestern University, Evanston, IL (US)

(72) Inventors: Armando Hernandez-Garcia, Chicago, IL (US); Samuel I. Stupp, Chicago, IL (US); Zaida Alvarez Pinto, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/476,083

(22) Filed: Mar. 31, 2017

(65) Prior Publication Data

US 2017/0283467 A1    Oct. 5, 2017

Related U.S. Application Data

(60) Provisional application No. 62/317,100, filed on Apr. 1, 2016.

(51) Int. Cl.
| | | |
|---|---|---|
| C07K 14/00 | (2006.01) | |
| C12N 15/11 | (2006.01) | |
| C12N 15/113 | (2010.01) | |
| C07K 7/08 | (2006.01) | |
| C07K 14/47 | (2006.01) | |

(52) U.S. Cl.
CPC .............. C07K 14/003 (2013.01); C07K 7/08 (2013.01); C07K 14/4723 (2013.01); C12N 15/111 (2013.01); C12N 15/113 (2013.01); C07K 2319/09 (2013.01); C07K 2319/10 (2013.01); C07K 2319/735 (2013.01); C07K 2319/85 (2013.01); C12N 2310/14 (2013.01); C12N 2310/3513 (2013.01); C12N 2310/3517 (2013.01); C12N 2320/32 (2013.01)

(58) Field of Classification Search
CPC .... A61K 9/51; A61K 49/0093; C12N 15/111; C12N 15/113; C07K 14/003
See application file for complete search history.

(56) References Cited

U.S. PATENT DOCUMENTS

| | | |
|---|---|---|
| 8,273,867 B2 | 9/2012 | Dowdy et al. |
| 8,822,663 B2 | 9/2014 | Schrum et al. |
| 2009/0093026 A1 | 4/2009 | Dowdy et al. |
| 2011/0207799 A1 | 8/2011 | Rozema et al. |
| 2012/0251618 A1 | 10/2012 | Schrum et al. |
| 2014/0294727 A1 | 10/2014 | Narasimhaswamy et al. |

FOREIGN PATENT DOCUMENTS

| | | |
|---|---|---|
| WO | WO 2010129853 | 11/2010 |
| WO | WO 2015061409 | 4/2015 |

OTHER PUBLICATIONS

Chou et al., Cancer Gene Ther., Oct. 2011 ; 18(10): 707-716. (Year: 2011).*
Dhar et al., Platinum and Other Heavy Metal Compounds in Cancer Chemotherapy, edited by Bonetti et al., 2009. (Year: 2009).*
Choi et al., Chimeric capsid protein as a nanocarrier for siRNA delivery: stability and cellular uptake of encapsulated siRNA. ACS Nano. Nov. 22, 2011;5(11):8690-9.
Dado et al., Redox control of secondary structure in a designed peptide. J Am Chem Soc.. Dec. 1, 2012; 115:12609-10.
Eguchi et al., Efficient siRNA delivery into primary cells by a peptide transduction domain-dsRNA binding domain fusion protein. Nat Biotechnol. Jun. 2009;27(6):567-71.
Kanasty et al., Delivery materials for siRNA therapeutics. Nat Mater. Nov. 2013;12(11):967-77.
Kim et al., Intracellular small interfering RNA delivery using genetically engineered double-stranded RNA binding protein domain. J Gene Med. Sep. 2009;11(9):804-12.
Kumar et al., Transvascular delivery of small interfering RNA to the central nervous system. Nature. Jul. 5, 2007;448(7149):39-43.
Ren et al., Targeted tumor-penetrating siRNA nanocomplexes for credentialing the ovarian cancer oncogene ID4. Sci Transl Med. Aug. 15, 2012;4(147):147ra112.
Wang et al., Reversible redox reconfiguration of secondary structures in a designed peptide. Angew Chem Int Ed Engl. Nov. 26, 2012;51(48):12099-101.
Wittrup et al., Knocking down disease: a progress report on siRNA therapeutics. Nat Rev Genet. Sep. 2015;16(9):543-52.

\* cited by examiner

*Primary Examiner* — Kaipeen E Yang

(74) *Attorney, Agent, or Firm* — Casimir Jones SC; David W. Staple

(57) ABSTRACT

Provided herein are polypeptides that self-assemble into nanoparticles upon binding to nucleic acids. The nanoparticles find use, for example in the delivery of the nucleic acids into cells.

15 Claims, 29 Drawing Sheets

Specification includes a Sequence Listing.

FIG. 2A
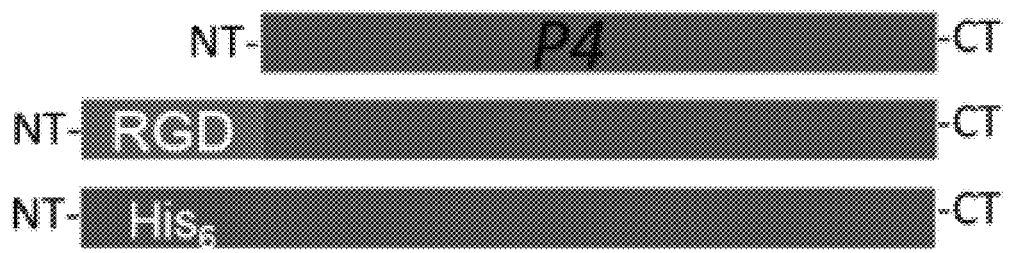
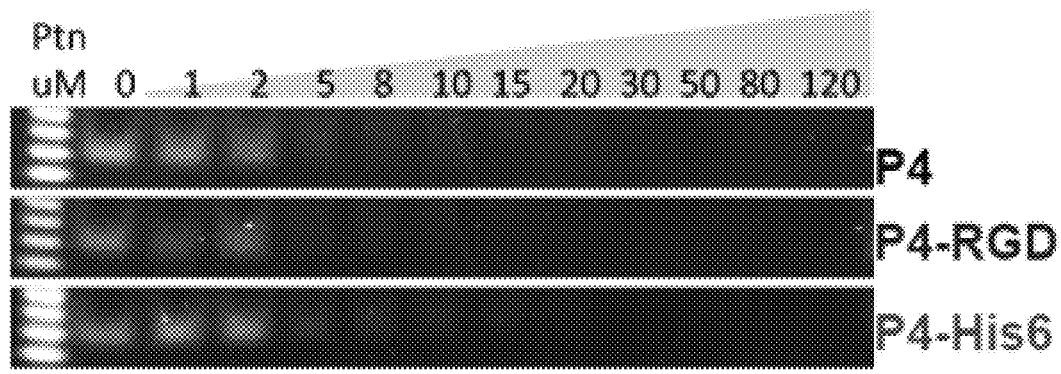
FIG. 2B

PROGRAMMABLE POLYPEPTIDE AND NUCLEIC ACID NANOPARTICLES

CROSS REFERENCE TO RELATED APPLICATIONS

The present application claims the priority benefit of U.S. Provisional Patent Application 62/317,100, filed Apr. 1, 2016, which is incorporated by reference in its entirety.

FIELD

Provided herein are polypeptides that self-assemble into nanoparticles upon binding to nucleic acids. The nanoparticles find use, for example in the delivery of the nucleic acids into cells.

BACKGROUND

Development of transfection tools is of great relevance, and especially for hard to transfect cells such as primary neuronal cultures.

SUMMARY

In some embodiments, provided herein are polypeptides comprising an assembly domain and a nucleic-acid-binding domain (NABD), wherein upon binding of the NABD to a nucleic acid to form a polypeptide/nucleic acid complex, the assembly domain facilitates self-assembly of the polypeptide/nucleic acid complex into nanoparticles.

In some embodiments, the assembly domain lacks secondary structure in the absence of complex formation between the NABD and a nucleic acid. In some embodiments, the assembly domain forms secondary structure with assembly domains of adjacent polypeptide in the presence of complex formation between the NABD and nucleic acids. In some embodiments, the secondary structure comprises beta-sheet interactions. In some embodiments, the assembly domain forms supramolecular interactions with assembly domains of adjacent polypeptide in the presence of complex formation between the NABD and nucleic acids. In some embodiments, the supramolecular interactions comprise hydrogen bonds. In some embodiments, the assembly domain is an oligomerization (e.g., dimerization) domain. In some embodiments, the assembly domain comprises a portion with at least 70% (e.g., 70%, 75%, 80%, 85%, 90%, 95%, 100%) sequence similarity with SEQ ID NO: 2. In some embodiments, the assembly domain comprises a portion with at least 70% (e.g., 70%, 75%, 80%, 85%, 90%, 95%, 100%) sequence identity with SEQ ID NO: 2. In some embodiments, the assembly domain comprises a portion with at least 70% (e.g., 70%, 75%, 80%, 85%, 90%, 95%, 100&) sequence similarity with SEQ ID NO: 12. In some embodiments, the assembly domain comprises a portion with at least 70% (e.g., 70%, 75%, 80%, 85%, 90%, 95%, 100%) sequence identity with SEQ ID NO: 12.

In some embodiments, the NABD binds DNA and/or RNA. In some embodiments, the NABD binds single-stranded (ss) and/or double-stranded (ds) nucleic acids. In some embodiments, the NABD comprises a portion with at least 70% (e.g., 70%, 75%, 80%, 85%, 90%, 95%, 100%) sequence similarity with SEQ ID NO: 3. In some embodiments, the NABD comprises a portion with at least 70% (e.g., 70%, 75%, 80%, 85%, 90%, 95%, 100%) sequence identity with SEQ ID NO: 3.

In some embodiments, the NABD and assembly domain are connected by a linker moiety. In some embodiments, the linker moiety is a peptide linker. In some embodiments, the peptide linker comprises GG. In some embodiments, the linker moiety is a non-peptide linker. In some embodiments, the non-peptide linker comprises polyethylene glycol.

In some embodiments, a polypeptide comprises at least 70% (e.g., 70%, 75%, 80%, 85%, 90%, 95%, 100%) sequence similarity with SEQ ID NO: 1. In some embodiments, a polypeptide comprises at least 70% (e.g., 70%, 75%, 80%, 85%, 90%, 95%, 100%) sequence identity with SEQ ID NO: 1. In some embodiments, a polypeptide comprises at least 70% (e.g., 70%, 75%, 80%, 85%, 90%, 95%, 100%) sequence similarity with SEQ ID NO: 11. In some embodiments, a polypeptide comprises at least 70% (e.g., 70%, 75%, 80%, 85%, 90%, 95%, 100%) sequence identity with SEQ ID NO: 11.

In some embodiments, a polypeptide further comprises a bioactive domain. In some embodiments, the bioactive domain enhances one or more characteristics selected from the group consisting of cell internalization, cell-targeting, endosome escape, and nuclear delivery. In some embodiments, the bioactive domain is selected from the group consisting of SEQ ID NO: 6, SEQ ID NO: 8, and SEQ ID NO: 10. In some embodiments, a polypeptide comprises at least 70% e.g., 70%, 75%, 80%, 85%, 90%, 95%, 100%) sequence similarity with SEQ ID NO: 6. In some embodiments, a polypeptide comprises at least 70% e.g., 70%, 75%, 80%, 85%, 90%, 95%, 100%) sequence identity with SEQ ID NO: 6. In some embodiments, a polypeptide comprises at least 70% e.g., 70%, 75%, 80%, 85%, 90%, 95%, 100%) sequence similarity with SEQ ID NO: 8. In some embodiments, a polypeptide comprises at least 70% e.g., 70%, 75%, 80%, 85%, 90%, 95%, 100%) sequence identity with SEQ ID NO: 8. In some embodiments, a polypeptide comprises at least 70% e.g., 70%, 75%, 80%, 85%, 90%, 95%, 100%) sequence similarity with SEQ ID NO: 10. In some embodiments, a polypeptide comprises at least 70% e.g., 70%, 75%, 80%, 85%, 90%, 95%, 100%) sequence identity with SEQ ID NO: 10.

In some embodiments, provided herein are carrier nanoparticles comprising: (a) cargo nucleic acids, and (b) polypeptides described herein. In some embodiments, the cargo nucleic acid is a DNA. In some embodiments, the cargo nucleic acid is an RNA. In some embodiments, the cargo nucleic acid is double stranded. In some embodiments, the cargo nucleic acid is single stranded. In some embodiments, each polypeptide present in the nanoparticle is bound to a cargo nucleic acid. In some embodiments, binding of the polypeptide to the cargo nucleic acid facilitates self-assembly of the polypeptide/nucleic acid complexes into the carrier nanoparticles. In some embodiments, the nanoparticle is between 20 and 800 nm in diameter (e.g., 20 nm, 30 nm, 40 nm, 50 nm, 75 nm, 100 nm, 150 nm, 200 nm, 250 nm, 300 nm, 400 nm, 500 nm, 600 nm, 700 nm, 800 nm, or any ranges there between). In some embodiments, the nanoparticle is readily internalized by cells (e.g., neuronal cells). In some embodiments, the nanoparticles disassemble, degrade, and/or release the nucleic acid cargo within cells.

In some embodiments, provided herein are methods of delivering a cargo nucleic acid into a cell, comprising exposing the cell to a nanoparticle described herein. In some embodiments, the cargo nucleic acid is selected from the group consisting of: an expression vector, a plasmid, an siRNA, a miRNA, an antisense oligonucleotide, crRNA, tracrRNA, sgRNA, and a Cas9-encoding RNA. In some embodiments, the cargo nucleic acid is delivered to the cell to: express a gene product from the cargo nucleic acid, inhibit expression of a gene within the cell, or alter the sequence of the genomic DNA within the cell.

BRIEF DESCRIPTION OF THE DRAWINGS

FIGS. 1A-I. Nanoparticles of an engineered polypeptide carrying siRNA (A) C-terminus RNA binding motif CT-dsRBD (in yellow) excised from a canonical double stranded RNA binding domain (dsRBD) and fused to a self-assembly enhancer μ-helix in order to obtain the engineered RNA binding polypeptide (P4) (B) electrophoresis gels of proteins binding siRNA (left). Plot of the bound siRNA (right). (C) Structural change of P4 and CT-dsRBD upon binding to siRNA determined by circular dichroism. (D) Increase in hydrodynamic size of P4 upon siRNA binding determined by DLS. (E) siRNA-P4 nanoparticles in solution imaged by cryo-TEM. Scale bar is 200 nm. (F) P4 is an unstructured polypeptide that self-assembles into nanoparticles upon binding to siRNA. (G) Enzymatic protection given by P4 nanoparticles. (H) Salt stability of P4 nanoparticles. (I) Formation of siRNA-P4 nanoparticles in different buffers.

FIGS. 2A-J. Programmable protein for bioactive siRNA delivery nanoparticles. (A) P4 is functionalized with bioactive peptides, P4-RGD & P4-His6. (B & C) Functionalized P4-RGD & P4-His6 bind to siRNA similarly as P4. (D) Structural change of functionalized P4-RGD & P4-His6 is triggered by siRNA binding as in P4. (E) Ellipticity change in function of siRNA concentration (bottom scale) and P4-to-siRNA stoichiometry (top scale). (F) Hydrodynamic size and (G) Zeta potential of P4 nanoparticles. (H & I) Cryo-TEM and (j) AFM micrographs of siRNA-P4 nanoparticles.

DEFINITIONS

Figure 1A:
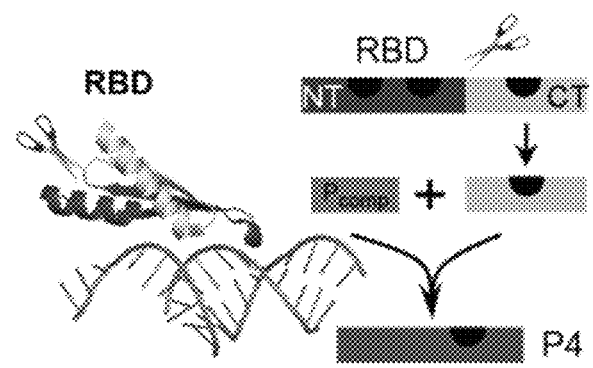

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a polypeptide" is a reference to one or more polypeptides and equivalents thereof known to those skilled in the art, and so forth.

As used herein, the term "nanoparticle" refers to a particle having dimensions between 1 and 1000 nanometers. A nanoparticle may or may not exhibit one or more size-related properties that differ significantly from those observed in larger particles or bulk materials.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile* or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 25 amino acids or less in length. A peptide may comprise natural amino acids, non-natural amino acids, amino acid analogs, and/or modified amino acids.

As used herein, the term "polypeptide" refers a polymer of amino acids, linked together by peptide bonds, that is over about 25 amino acids or less in length. A polypeptide may comprise natural amino acids, non-natural amino acids, amino acid analogs, and/or modified amino acids.

As used herein, the term "artificial" refers to compositions and systems that are designed or prepared by man, and are not naturally occurring. For example, an artificial peptide or nucleic acid is one comprising a non-natural sequence (e.g., a polypeptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions (e.g., not conservative or semi-conservative) involve the exchange of an amino acid of one class or group for an amino acid from another class or group.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative (e.g., "conservative sequence similarity") and/or semi-conservative (e.g., "semi-conservative sequence similarity") amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, and the length of the comparison window is not specified, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, and the length of the comparison window is not specified, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least Y % sequence identity with SEQ ID NO:Z" may have up to X substitutions relative to SEQ ID NO:Z, and may therefore also be expressed as "having X or fewer substitutions relative to SEQ ID NO:Z."

As used herein, the term "physiological conditions" encompasses any conditions compatible with living cells, e.g., predominantly aqueous conditions of a temperature, pH, salinity, chemical makeup, etc. that are compatible with living cells.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Sample may also refer to cell lysates or purified forms of the peptides and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, crystals and industrial samples. Such examples are not however to be construed as limiting the sample types applicable to the present invention.

As used herein, the term "supramolecular" (e.g., "supramolecular complex," "supramolecular interactions," "supramolecular fiber," "supramolecular polymer," etc.) refers to the non-covalent interactions between molecules (e.g., polymers, marcomolecules, etc.) and the multicomponent assemblies, complexes, systems, and/or fibers that form as a result.

As used herein, the terms "self-assemble" and "self-assembly" refer to formation of a discrete, non-random, aggregate structure from component parts (e.g., polypeptides and nucleic acids and/or complexes thereof); said assembly occurring spontaneously through random movements of the components (e.g. molecules) due only to the inherent chemical or structural properties and attractive forces of those components.

As used herein, the term "bioactive peptide" refers to amino acid sequences that mediate a bioactivity. Polypeptides, complexes, and structures (e.g., nanoparticles) bearing bioactive peptides exhibit the bioactivity of the bioactive peptide.

As used herein, the term "polypeptide/nucleic acid complex" ("P/NA complex") refers the intermolecular complex formed by the interaction (e.g., noncovalent binding) of a polypeptide (e.g., comprising a NA binding domain (e.g., RNA binding domain, DNA binding domain, etc.)) and a nucleic acid. A P/NA complex may comprise a single polypeptide and single nucleic acid ("1:1 P/NA complex"), a single polypeptide (e.g., comprising multiple NA binding domains) and multiple nucleic acids (e.g., "1:X P/NA complex", wherein X is the number of NA binding domains on the polypeptide and/or the number of nucleic acids bound by the polypeptide), or multiple polypeptides bound to a single nucleic acid (e.g., "X:1 P/NA complex").

DETAILED DESCRIPTION

Provided herein are polypeptides that self-assemble into nanoparticles upon binding to nucleic acids. The nanoparticles find use, for example in the delivery of the nucleic acids into cells.

I. General

The technology provided herein is based on an engineered polypeptide nanocarrier that binds to nucleic acids (NA) and is useful for the delivery thereof into cells (e.g., primary culture neuronal cells), particularly cells which have proven difficult to transfect by other technologies and/or require harsh or toxic treatment to facilitate nucleic acid transfection. In some embodiments, the polypeptides described herein lack significant secondary structure (e.g., as demonstrated by circular dichroism or other biophysical or biochemical techniques). In some embodiments, the polypeptides comprise a first peptide sequence that binds to cargo nucleic acids (e.g., nucleic acid binding domain (NABD)) and a second peptide sequence that promotes self-assembly (e.g., assembly domains (AD)) of polypeptide/nucleic acid (P/NA) complexes into nanoparticles. In some embodiments, the engineered artificial polypeptides also provide a scaffold that can be programmed with bioactive peptides in order to provide nanoparticles that exhibit particular enhanced functionalities, such as cell internalization, specific cell targeting, endosome escape, nuclear cargo delivery, etc. In some embodiments, the P/NA complexes are internalized by cells (e.g., brain-derived cells and other cell lines, in vivo cells, etc.) with high efficiency and low toxicity, thereby effectively triggering the biological effect of the NA.

Experiments were conducted during development of embodiments herein to develop and test polypeptides capable of delivery of nucleic acids (e.g., siRNA and other therapeutic nucleic acids) into cells, especially difficult to transfect cells such as neuronal cells. In some embodiments, polypeptides were prepared from the RNA binding domain of a natural dsRNA-binding protein fused to a designed peptide. The resultant polypeptide is a short, hydrophilic, random coil in solution which becomes folded when bound to nucleic acids (e.g., siRNA) to form a polypeptide/nucleic acid complex. The polypeptide/nucleic acid complex (P/NA complex) self-assembles into nanoparticles and provides chemical stability and protection against enzymatic degradation (e.g., to the polypeptide and/or nucleic acid).

Experiments conducted during development of embodiments herein demonstrated that when P/NA complex nanoparticles (e.g., comprising an siRNA) are incubated with cells, the nanoparticles are internalized by the cells and escape endosomes into the cytosol, decreasing the expression of the targeted mRNA. Internalization, gene knockdown, and toxicity of the nanoparticles were tested in human lung carcinoma cell line and mice primary cortical astrocytes and neuron cell cultures. The nanoparticles showed superior internalization and gene expression knockdown than commercial positive controls and also less toxicity even when used at high concentrations.

The targeting, cell-entry, endosome-escape, and subcellular-localization properties of the P/NA complex nanoparticles are programmable by the addition of bioactive moieties (e.g., peptide sequences) without disturbing the general physical chemical properties of the nanoparticles and siRNA delivery.

II. Assembly Domains (AD)

The polypeptides provided herein comprise an assembly domain that facilitates self-assembly of the polypeptide/nucleic acid complexes into nanoparticles. In some embodiments, assembly domains interact with the assembly domains of like polypeptides. In some embodiments, the interaction between ADs is enhanced upon binding of the polypeptide (NABD) to a nucleic acid. In some embodiments, ADs facilitate the folding and/or aggregation of P/NA complexes into nanoparticles. In some embodiments, ADs facilitate the non-covalent oligomerization of P/NA complexes and subsequence formation of nanoparticles.

In some embodiments, ADs are 5-40 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or ranges there between) amino acids in length.

In some embodiments, ADs are unstructed domains that adopt secondary structure elements that facilitate self-assembly of the polypeptides upon binding of the NABD of the polypeptides to nucleic acids.

In some embodiments, ADs are dimerizable and/or oligomerizable peptides. In some embodiments, the affinity between the ADs is greatly enhanced (e.g., 2-fold, 3-fold, 4-fold, 5-fold, 10-fold, 20-fold, 50-fold, 100-fold, $10^3$-fold, $10^4$-fold, $10^5$-fold, $10^6$-fold, or ranges there between) upon binding of an associated NABD to a nucleic acid.

In some embodiments, ADs are peptides that form aggregates with like peptides. In some embodiments, the capacity to aggregate with like peptides is greatly enhanced (e.g., 2-fold, 3-fold, 4-fold, 5-fold, 10-fold, 20-fold, 50-fold, 100-fold, $10^3$-fold, $10^4$-fold, $10^5$-fold, $10^6$-fold, or ranges there between) upon binding of an associated NABD to a nucleic acid.

In some embodiments, the assembly domain is derived from a peptide described in Wang, X. et. al. Angew. Chem., 124, 2012: incorporated by reference in its entirety (e.g., SEQ ID NO: 2). In some embodiments, polypeptides comprising such an AD will self-assemble into nanoparticles upon interaction of the polypeptides with cargo nucleic acids. In some embodiments, the AD comprises at least 70% (e.g., 70%, 75%, 80%, 85%, 90%) sequence identity or similarity with SEQ ID NO: 2. In some embodiments, the AD comprises fewer than 5 substitutions relative to SEQ ID NO: 2.

In some embodiments, the assembly domain is derived from a peptide described in Dado and Gellman, J. am. Chem. Soc. 1993, 115, 12609-10: incorporated by reference in its entirety (e.g., SEQ ID NO: 12). In some embodiments, polypeptides comprising such an AD will self-assemble into nanoparticles upon interaction of the polypeptides with cargo nucleic acids. In some embodiments, the AD comprises at least 70% (e.g., 70%, 75%, 80%, 85%, 90%) sequence identity or similarity with SEQ ID NO: 12. In some embodiments, the AD comprises fewer than 5 substitutions relative to SEQ ID NO: 12.

III. Nucleic Acid Binding Domains (NABD)

The polypeptides provided herein comprise a nucleic acid binding domain that facilitates interaction (e.g., binding) of the polypeptide with cargo nucleic acids.

In some embodiments, the NABD is derived from a natural nucleic acid binding protein. In some embodiments, NABD comprises the portion of a natural nucleic acid binding protein that is responsible for nucleic acid binding.

In some embodiments, the NABD is derived from a natural RNA binding protein. Exemplary RNA binding proteins include histone, RDE-4 protein, or protamine. Protamines are arginine-rich proteins and include, for example, a sequence RSRRRRRRSCQTRRR (SEQ ID NO: 95). Additional dsRNA binding proteins and their Accession numbers in parenthesis include: PKR (AAA36409, AAA61926, Q03963), TRBP (P97473, AAA36765), PACT (AAC25672, AAA49947, NP609646), Staufen (AAD17531, AAF98119, AAD17529, P25159), NFAR1 (AF167569), NFAR2 (AF167570, AAF31446, AAC71052, AAA19960, AAA19961, AAG22859), SPNR (AAK20832, AAF59924, A57284), RHA (CAA71668, AAC05725, AAF57297), NREBP (AAK07692, AAF23120, AAF54409, T33856), kanadaptin (AAK29177, AAB88191, AAF55582, NP499172, NP198700, BAB19354), HYL1 (NP563850), hyponastic leaves (CAC05659, BAB00641), ADAR1 (AAB97118, P55266, AAK16102, AAB51687, AF051275), ADAR2 P78563, P51400, AAK17102, AAF63702), ADAR3 (AAF78094, AAB41862, AAF76894), TENR (XP059592, CAA59168), RNaseIII (AAF80558, AAF59169, Z81070Q02555/S55784, P05797), and Dicer (BAA78691, AF408-401, AAF56056, S44849, AAF03534, Q9884), RDE-4 (AY071926), FLJ20399 (NP060273, BAB26260), CG1434 (AAF48360, EAA12065, CAA21662), CG13139 (XP059208, XP143416, XP110450, AAF52926, EEA14824), DGCRK6 (BAB83032, XP110167) CG1800 (AAF57175, EAA08039), FLJ20036 (AAH22270, XP134159), MRP-L45 (BAB14234, XP129893), CG2109 (AAF52025), CG12493 (NP647927), CG10630 (AAF50777), CG17686 (AAD50502), T22A3.5 (CAB03384) and accession number EAA14308. The sequences of such binding proteins are known in the art based upon the accession numbers. The sequences associated with said accession numbers are specifically incorporated herein by reference in their entireties. In some embodiments, NABD comprise at least 70% (e.g., 70%, 75%, 80%, 85%, 90%) sequence identity or similarity with one of the aforementioned RNA binding proteins, the RNA binding domains thereof, and/or a fragment thereof.

In some embodiments, the NABD comprises a DNA-binding domain and/or a structure known to facilitate interactions/binding to DNA. Such DNA-binding domains may be selected from: helix-turn-helix, zinc finger, leucine zipper, winged helix, winged helix-turn-helix, helix-loop-helix, HMG-box, Wor3 domain, OB-fold domain, immunoglobulin fold, B3 domain, TAL effector DNA-binding domain, RNA-guided DNA-binding domain, etc.

In some embodiments, the NABD comprises an RNA-binding domain and/or a structure known to facilitate interactions/binding to RNA. Such RNA-binding domains may be selected from: RNA-recognition motif (RRM), double-stranded RNA binding motif (dsRBM), zinc fingers, etc.

In some embodiments, the NABD comprises at least 70% (e.g., 70%, 75%, 80%, 85%, 90%, 95%, 100%) sequence identity or similarity with SEQ ID NO: 3. In some embodiments, the AD comprises fewer than 5 substitutions relative to SEQ ID NO: 3.

IV. Linkers (L)

In some embodiments, the NABD and AD are directly connected (e.g., via a peptide bond). However, in other embodiments, the NABD and AD are linked via a linker (e.g., peptide linker or non-peptide linker). In some embodiments, the presence of the linker does not substantially affect the function of the groups in connects (e.g., NABD and AD).

In some embodiments, a linker is a peptide linker (e.g., SEQ ID NO: 4 and SEQ ID NO: 1). A peptide linker is 1-2, 1-4, 1-6, 1-8, 1-10, 1-20, or 1-50 amino acids in length. In some embodiments, a peptide linker comprises any suitable combination of natural amino acids. In some embodiments, a peptide linker comprises any suitable combination of natural amino acids, unnatural amino acids, and/or amino acid analogs. In some embodiments, a peptide linker connects two other peptide domains (e.g., NABD, AD, bioactive peptide) via the peptide backbone of the linker and the connected groups.

In some embodiments, a linker is a non-peptide linker (e.g., SEQ ID NO: 11). Suitable non-peptide linkers include substituted and non-substituted alkyl chains, and non-peptide polymers.

Suitable non-substituted alkyl chains include, for example, linear or branched carbon chains of 1-50 carbons (e.g., 1, 2, 3, 4, 5, 6, 7, 8, 9, 10, 14, 18, 22, 26, 30, 34, 38, 42, 46, 50, or ranges there between).

Suitable non-substituted alkyl chains include, for example, linear or branched carbon chains of 1-50 carbons (e.g., 1, 2, 3, 4, 5, 6, 7, 8, 9, 10, 14, 18, 22, 26, 30, 34, 38, 42, 46, 50, or ranges there between) in which one or more positions in the carbon chain are substituted for a S, N, or O atom, and/or one or more organic functional groups are appended onto the chain or inserted within it (e.g., —NH—(CH$_2$)$_x$—COO—, —NH(CH2)x((CH2)2COO)y-(CH2)zCOO—, etc.).

Suitable non-peptide polymers for sue as linkers herein polyethylene glycol (e.g., PEG10), polypropylene glycol, copolymers of ethylene glycol and propylene glycol, polyoxyethylated polyols, polyvinyl alcohol, polysaccharides, dextran, polyvinyl ethyl ether, PLA (polylactic acid, polylactic acid) and PLGA (poly lactic-glycolic acid, polylactic-glycolic acid) biodegradable polymer, lipid polymer, chitin acids, etc. Derivatives of these polymers which can be prepared by those of skill in the art are also included in the scope herein.

In some embodiments, a linker (e.g., peptide linker or non-peptide linker) links a bioactive moiety (e.g., bioactive peptide, bioactive group) to a polypeptide (e.g., to an NABD, to an AD). In the case of non-peptide linkers, the linker may be attached to the backbone or a sidechain of the polypeptide.

V. Bioactive Moieties

In some embodiments, polypeptides herein comprise a bioactive moiety (e.g., peptide bioactive domain, non-peptide bioactive group), that imparts a particular functionality to the nanoparticles formed from complexes of the polypeptides and nucleic acid cargos. In some embodiments, the bioactivity facilitates one or more aspects of cellular internalization of the nucleic acid cargo. For example, in some embodiments, a bioactive moiety (e.g., ligand for cell surface receptor, antibody, antibody fragment, etc.) facilitates extracellular targeting (e.g., delivery of nanoparticles to a specific tissue, cell type, etc.). In some embodiments, a bioactive moiety e.g., cell-penetrating peptides, ligand for cell surface receptor, etc.) facilitates cellular uptake of the nanoparticles into cells. In some embodiments, a bioactive moiety facilitates endosomal escape following cellular uptake. In some embodiments, a bioactive moiety facilitates subcellular localization of the NA cargo (e.g., to the cytosol, nuclear localization, transport to a specific subcellular compartment). In some embodiments, a bioactive moiety enhances the cellular function of the NA cargo (e.g., RNAi, CRISPR, genomic integration, gene expression, gene therapy, etc.).

In some embodiments, the bioactive moiety is a targeting moiety (e.g., targeting domain or peptide). In some embodiments, the bioactive moiety facilitates extracellular targeting and/or subcellular localization.

In some embodiments, a targeting peptide comprises an NLS. In some embodiments, the NLS comprises a fragment of a protein selected from the group consisting of SV40 large T NLS, M9 NLS, c-myc NLS, nucleoplasmin NLS, *Xenopus* N1 NLS, FGF3 NLS, and PARP NLS, or a variant having at least 70% (e.g., 70%, 75%, 80%, 85%, 90%, 95%, 100%, or ranges there between) sequence identity and/or similarity to such a fragment. Exemplary NLS targeting peptides include those having at least 70% (e.g., 70%, 75%, 80%, 85%, 90%, 95%, 100%, or ranges there between) sequence identity and/or similarity to SEQ ID NOS: 13-22.

In some embodiments, the bioactive peptide comprises a fusogenic peptide. In some embodiments, the fusogenic peptide comprises a fragment of a protein selected from the group consisting of melittin, HA-2, HSWYG, GAL4, KALA, JST-1, ppTG-1, VSV, penetratin, and transportan, or a variant having at least 70% (e.g., 70%, 75%, 80%, 85%, 90%, 95%, 100%, or ranges there between) sequence identity and/or similarity to such a fragment. Exemplary fusogenic targeting peptides include those having at least 70% (e.g., 70%, 75%, 80%, 85%, 90%, 95%, 100%, or ranges there between) sequence identity and/or similarity to SEQ ID NOS: 23-33.

In some embodiments, the bioactive peptide comprises a receptor ligand. In some embodiments, suitable receptor ligand peptides include those having at least 70% (e.g., 70%, 75%, 80%, 85%, 90%, 95%, 100%, or ranges there between) sequence identity and/or similarity SEQ ID NOS: 34-55.

In some embodiments, the bioactive peptide is a peptide hormone. Exemplary peptide hormones include those having at least 70% (e.g., 70%, 75%, 80%, 85%, 90%, 95%, 100%, or ranges there between) sequence identity and/or similarity to SEQ ID NOS: 56-79.

In some embodiments, the bioactive peptide comprises an antimicrobial peptide. In some embodiments, the antimicrobial peptide comprises a fragment of a protein selected from the group consisting of: Abaecin, Apidaecins, Bac-5, Bac-7, Drosocin, Phosphenin, α-Defensins, β-Defensins, Insect defensins, Plant defensins, Protegrins, Drosomycin, Amphiphilic α-helical structure: Magainins, Dermaseptins, Bombinin, Cecropin, Esculentins-1, and Esculentins-2, or a variant having at least 70% (e.g., 70%, 75%, 80%, 85%, 90%, 95%, 100%, or ranges there between) sequence identity and/or similarity to such fragments. Exemplary antimicrobial peptides include those having at least 70% (e.g., 70%, 75%, 80%, 85%, 90%, 95%, 100%, or ranges there between) sequence identity and/or similarity to SEQ ID NOS: 80-94.

In some embodiments, the bioactive peptide comprises an integrin binding peptide. In some embodiments, suitable integrin binding peptides include those having at least 70% (e.g., 70%, 75%, 80%, 85%, 90%, 95%, 100%, or ranges there between) sequence identity and/or similarity SEQ ID NO: 6.

In some embodiments, the bioactive peptide comprises an endosomal escape peptide. In some embodiments, suitable integrin endosomal escape peptides include those having at least 70% (e.g., 70%, 75%, 80%, 85%, 90%, 95%, 100%, or ranges there between) sequence identity and/or similarity SEQ ID NO: 8.

In some embodiments, a bioactive peptide is a variant of a natural peptide or a variant of a fragment of a natural polypeptide. In some embodiments, a bioactive peptide comprises conservative, semi-conservative, and/or nonconservative substitutions (e.g., 1, 2, 3, 4, 5, 6, 7, 8, 9, 10, or more, or ranges there between) with respect to a natural sequence. In some embodiments, in which a bioactive peptide is 24 amino acid residues or less in length, the bioactive peptide has 1-6 amino acid substitutions relative to a natural sequence. In some embodiments, a bioactive peptide is a natural sequence or a fragment of a natural sequence.

Experiments conducted during development of embodiments herein indicate that polypeptides comprising a bioactive peptide in addition to the NABD and AD (and linker) bind nucleic acid cargo and form nanoparticles in a similar manner and to a similar degree as polypeptides comprising NABD and AD (and linker) alone.

VI. Polypeptides

In some embodiments, provided herein are polypeptides that self-assemble into nanoparticles upon binding to a cargo nucleic acid. In some embodiments, the polypeptides comprise a nucleic acid binding domain and an assembly domain. In some embodiments, the polypeptides optionally also comprise one or more bioactive moieties. In some embodiments, the polypeptides comprise a linker connecting the NABD and AD. In some embodiments, when present, the one or more bioactive peptides are connected to each other and or an NABD and/or AD by a linker.

In some embodiments, embodiments are provided comprising any suitable arrangement of the constituent domains/moieties of the polypeptides herein. For example, the following arrangements are within the scope herein: AD-NABD, NABD-AD, Bioactive-AD-NABD, Bioactive-NABD-AD, AD-NABD-Bioactive, NABD-AD-Bioactive, AD-Bioactive-NABD, NABD-Bioactive-AD, Bioactive1-AD-NABD-Bioactive2, Bioactive1-AD-Bioactive2-NABD, AD-Bioactive-NABD-Bioactive2, Bioactive1-Bioactive2-AD-NABD, AD-NABD-Bioactive1-Bioactive2, etc. In any of these arrangements, the listed domains/moieties may be connected directly (e.g., via peptide bond) or may be connected through a linker. Further, additional domains/moieties may be included (e.g., additional bioactive moieties, additional NABPs, additional ADs, etc.).

In some embodiments, a polypeptide comprises two or more (e.g., 2, 3, 4, 5, 6, 7, 8, 9 10, or more) NABDs and/or two or more (e.g., 2, 3, 4, 5, 6, 7, 8, 9 10, or more) ADs. In such embodiments, the multiple NABDs and/or multiple ADs may be grouped together (e.g., linked consecutively (e.g., directly or by a linker)), or may have other domains/moieties interspersed (e.g., NABD1-Bioactive-NABD2-AD-NABD3, etc.).

VII. Nucleic Acid Cargo

In some embodiments, polypeptides herein are engineered to bind to (e.g., non-covalently) a nucleic acid cargo molecule. In some embodiments, polypeptides comprise a NABD that generically binds all nucleic acid species, is specific for DNA or RNA, is specific for double-stranded nucleic acid (dsNA), is specific for single-stranded nucleic acid (ssNA), is specific for a particular NA secondary or tertiary structure (e.g., hairpin, triplex, pseudoknot, etc.), and/or is specific for a particular nucleotide sequence. In some embodiments, any nucleic acid may find use as cargo for the appropriately-paired polypeptide (e.g., with the appropriate NABD).

In some embodiments, nucleic acids that find use in embodiments herein include, but are not limited to: cDNA, genomic DNA, mRNA, siRNA, shRNA, miRNA, antisense RNA, ribozymes, catalytic DNA, triple helix RNA, aptamers, vectors, combinations/hybrids thereof, and the like.

In some embodiments, a nucleic acid is engineered to contain a sequence that is particularly amenable to binding by a particular NABD. In some embodiments, a nucleic acid comprises one or more (e.g., 1, 2, 3, 4, 5, 6, 7, 8, 9, 10, or more) NABD interaction elements (e.g., sequences, structures, etc.). In some embodiments, the presence of multiple NABD interaction elements on a cargo NA allows for interaction with multiple polypeptide described herein. In some embodiments, the ratio of NABDs on a polypeptide to the number of NABD interaction elements on a cargo NA provides for tuning of the poypeptide to NA ratio within the resulting nanoparticle.

In some embodiments, a nucleic acid lacks any sequence or structure that makes it particularly amenable to use in embodiments herein, but nonetheless finds use in embodiments herein (e.g., with a general NABD).

VIII. Nanoparticles

In some embodiments, provided herein are nanoparticles of polypeptide and nucleic acid complexes. In some embodiments, P/NA complex nanoparticles serve as carriers for nucleic acid cargo molecules and allow for the efficient delivery of the nucleic acids into cells.

In some embodiments, upon non-covalently binding to a nucleic acid cargo, the polypeptides interact with one another to self-assemble into nanoparticles. In some embodiments, the binding of the nucleic acid by the NABD of the polypeptide triggers self-assemble of the nanoparticles. In some embodiments, binding of the nucleic acid by the NABD triggers a structural change in the AD, which drives self-assembly of the nanoparticles. In some embodiments, the association of the negatively-charged nucleic acid with the polypeptide drives the self-assembly. The embodiments described herein are not limited to any particular mechanism of self-assembly and an understanding of the mechanism of self-assembly is not necessary to practice such embodiments.

In some embodiments, the nanoparticles comprise, consist essentially of, or consist of polypeptide and nucleic acid. In some embodiments, the nanoparticles comprise, consist essentially of, or consist of polypeptide, nucleic acid, and components from the solution containing the polypeptide and nucleic acid components (e.g., buffer, salt, etc.).

In some embodiments, the nanoparticles are non-toxic to cells.

In some embodiments, the nanoparticles are spherical or substantially spherical (e.g., having all cross-sectional dimensions within 5% of each other). In some embodiments, the nanoparticles are irregularly shaped. In some embodiments, the nanoparticles are 20-800 nm in diameter (e.g., 20 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 350 nm, 400 nm, 500 nm, 600 nm, 700 nm, 800 nm, or any ranges there between).

IX. Methods/Applications

In some embodiments, provided herein are methods of delivering/introducing nucleic acids into cells. In some embodiments, cargo nucleic acids having particular characteristics (e.g., siRNA, encoding a gene, etc.) are delivered to cells in order to elicit a desired response (e.g., alter the genome of the cell, express a gene, knockout a gene, etc.).

The polypeptides, P/NA complexes, nanoparticles, kits, and methods described herein find use in any suitable applications or technologies in which it is desirable to introduce a nucleic acid into a cell or population of cells. Embodiments herein find use in therapeutic (e.g., medical, veterinary, etc.) and research applications. For example, embodiments herein may find use: in the transfection of siRNA and other nucleic acids (e.g., single hairpin RNA, messenger RNA, plasmid DNA, etc.) into cell lines and cultured cell (e.g., cancer cell lines, primary brain-derived cells, etc.), as a molecular tool for biology (e.g., knockdown specific genes in genomic and genetic research), as a nucleic acid carrier of therapeutic nucleic acids to promote the knockdown of specific genes, to treat or prevent diseases (e.g., via delivery of nucleic acid therapeutics to cells in vivo (e.g., neuronal and/or brain-based cells)), for genetic-based regenerative medicine, in therapeutic gene therapy, etc.

In some embodiments, methods herein find use with cells in vivo, in vitro, in situ, in whole animals (e.g., human patients), etc. In some embodiments, any suitable cell types may be treated with the compositions and methods herein to introduce nucleic acids into the cells. Cell may be eukaryotic or bacterial. The cells may be any cell type, including, for example, a differentiated cell, a precursor cell, or a stem cell.

Some non-limiting examples of human or animal cells include an epithelial cell (including oral and gastrointestinal mucosal epithelia, urinary tract epithelia), endothelial cell, vascular endothelial cell, neural cell, epidermal cell, keratinocyte, melanocyte, osteoblast, intervertebral disc cell, chondrocyte, hepatocyte, pancreatic cell, hematopoietic cell, angioblast, B-cell, T-cell, erythrocyte, macrophage, monocyte, bone marrow mesenchymal cell, fibroblast, myoblast, muscle cell, cardiomyocyte, amniotic or placental cell, or stem cell.

The cell may be a stem cell. Types of stem cells include: undifferentiated stem cells, pluripotent stem cells, induced pluripotent stem cells or iPS cells, lineage-restricted stem cells, precursor cells, somatic stem cells, terminally differentiated somatic stem cells, cells expressing one or more markers of multilineage differentiation potential, cells expressing one or more markers of pluripotent stem cells, hematopoietic, neural, mesenchymal, postpartum, pancreatic, hepatic, retinal epithelial, olfactory bulb, endothelial, muscle, adipose-derived, ileac crest, bone marrow, periodontal ligament, oval and dermal stem cells and organ specific stem cells or progenitor cells, as well as embryonic stem cells.

In some embodiments, the cells are neural or brain-derived cells. Certain types of neural or brain-derived cells have proven particularly difficult to introduce nucleic acids into by conventional methods. However, in some embodiments, methods and compositions herein are particularly effecting in introducing nucleic acids into these cell types. Neural cells include those found in the central nervous system and peripheral nervous system. Neural or brain-derived cell types that find use as the targets of the nucleic-acid-introduction methods and compositions described herein include glial cells, such as astrocytes, oligodendrocytes, ependymal cells, radial glia cells, schwann cells, satellite glial cells, enteric glial cells, pituicytes, tanycytes, and microglia; and neurons.

In some embodiments, the cells are genetically engineered cells.

In some embodiments, methods and compositions herein find use in the delivery of a nucleic-acid-based therapeutic to a cell or subject. In some embodiments, a subject suffers from a genetic disorder and a nucleic acid is delivered to turn off a disease causing gene (e.g., by antisense, siRNA, ribozymes, or RNAi) or to cause expression of a therapeutic gene. In some embodiments, methods and compositions also find use in the treatment of acquired diseases (or diseases with both a genetic and environmental component), such as cancer, infectious disorders (AIDS), diabetes, heart disease, arthritis, and neurodegenerative disorders (Parkinson's and Alzheimer's).

X. Sequences

The following sequences find use in some embodiments herein, may be referenced above or in the claims, and are included in a sequence listing.

```
SEQ ID NO: 1-
SIRKLEYEIEELRLRIGGGTFVETGSGTSKQVAKRVAAEKLLTKFKT

SEQ ID NO: 2-
SIRKLEYEIEELRLRIG

SEQ ID NO: 3-
TFVETGSGTSKQVAKRVAAEKLLTKFKT

SEQ ID NO: 4-
GG

SEQ ID NO: 5-
CRGDCSIRKLEYEIEELRLRIGGGTFVETGSGTSKQVAKRVAAEKLL
TKFKT

SEQ ID NO: 6-
CRGDC

SEQ ID NO: 7-
HHHHHHSIRKLEYEIEELRLRIGGGTFVETGSGTSKQVAKRVAAEKL
LTKFKT

SEQ ID NO: 8-
HHHHHH

SEQ ID NO: 9-
CRGDCHHHHHHSIRKLEYEIEELRLRIGGGTFVETGSGTSKQVAKRV
AAEKLLTKFKT

SEQ ID NO: 10:-
CRGDCHHHHHH

SEQ ID NO: 11-
AMLKAMLKAMAELMAKLY-PEG10-TFVETGSGTSKQVAKRVAAEKL
LTKFKT

SEQ ID NO: 12-
AMLKAMLKAMAELMAKLY

SEQ ID NO: 13-
GGPKKKRKVEDPTG

SEQ ID NO: 14-
GGPKTKRKVEDPTG

SEQ ID NO: 15-
GGGGGGPKKRKVG

SEQ ID NO: 16-
KKKKKKPKKRKVG

SEQ ID NO: 17-
GGNQSSNFGPMKGGNFGGRSSGPYGGGQYFAKPRNQGGY

SEQ ID NO: 18-
GGPAAKRVKLD

SEQ ID NO: 19-
GGKRAATKKAGQAKKKK

SEQ ID NO: 20-
GGVRKKRKTEEESPLKDKDAKKSKQE

SEQ ID NO: 21-
GGRLRRDAGGRGGVYQHLGGAPRRRK

SEQ ID NO: 22-
GGKRKGDEVDGVDQCAKKSKK

SEQ ID NO: 23-
GGIGAVLKVLTTGLPALISWIKRKRQQ

SEQ ID NO: 24-
GGIGAVLKVLTTGLPALISWIKRKREE
```

-continued

SEQ ID NO: 25-
GGLFEAIAGFIENGWEGMINGWYG

SEQ ID NO: 26-
GGLFHAIAAHFIHGGWHGLIHGWWG

SEQ ID NO: 27-
GGWEAALAEALAEALAEHLAEALALEALEALEALAA

SEQ ID NO: 28-
GGWEAKLAKALAKALAKHLAKALAKALAKALAA

SEQ ID NO: 29-
GGLFEALLELLESLWELLLEA

SEQ ID NO: 30-
GGLFKALLKLLKSLWKLLLKA

SEQ ID NO: 31-
GGKFTIVFPHNQKGNWKNVPSNYHY

SEQ ID NO: 32-
GGREIKIWFENRRMKWKK

SEQ ID NO: 33-
GGWTLNSAGYLLGKINLKALAALAKKIL

SEQ ID NO: 34-
CDCRGDCFC

SEQ ID NO: 35-
CNGRC

SEQ ID NO: 36-
CPRECESIC

SEQ ID NO: 37-
CPGPEGAGC

SEQ ID NO: 38-
CTTHWGFTLC

SEQ ID NO: 39-
CRRHWGFEFC

SEQ ID NO: 40-
GLS

SEQ ID NO: 41-
CGRRAGGSC

SEQ ID NO: 42-
CVPELGHEC

SEQ ID NO: 43-
HTMYYHHYQHHL

SEQ ID NO: 44-
VHSPNKK

SEQ ID NO: 45-
CSRPRRSEC

SEQ ID NO: 46-
CRGRRST

SEQ ID NO: 47-
ICRRARGDNPDDRCT

SEQ ID NO: 48-
PLAEIDGIELTY

SEQ ID NO: 49-
HSDGTFTSELSRLRDSARLQRLLQGLV

SEQ ID NO: 50-
NPVVGYIGERPQYRDL

SEQ ID NO: 51-
CTTTHTFVKALTMDGKQAAWRFIRIDTAC

SEQ ID NO: 52-
ELYENKIPRRPYIL

SEQ ID NO: 53-
LSIPPKA

SEQ ID NO: 54-
FQTPPQL

SEQ ID NO: 55-
LTPATAI

SEQ ID NO: 56-
CYIQNCPLG

SEQ ID NO: 57-
VYFQNCPRG

SEQ ID NO: 58-
SYSMEHFRWGKPV

SEQ ID NO: 59-
AEKKDEGPYRMEHFRWGSPPKD

SEQ ID NO: 60-
YVMGHFRWDRFG

SEQ ID NO: 61-
SYSMEHFRWGKPVGKKRRPVKVYPNGAEDESAEAFPLEF

SEQ ID NO: 62-
SQEPPISLDLTFHLLREVLEMTKADQLAQQAHSNRKLLDIA

SEQ ID NO: 63-
EHWSYGLRPG

SEQ ID NO: 64-
EHP

SEQ ID NO: 65-
AGCKNFFWKTFTSC

SEQ ID NO: 66-
CSNLSTCVLGKLSQELHKLQTYPRTNTGSGTP

SEQ ID NO: 67-
HAEGTFTSDVSSYLEGQAAKEFIAWLVKGRG

SEQ ID NO: 68-
GSSFLSPEHQRVQQRKESKKPPAKLQPR

SEQ ID NO: 69-
FNAPFDVGIKLSGVQYQQHSQAL

SEQ ID NO: 70-
PGPWLEEEEEAYGWMDF

SEQ ID NO: 71-
HSDGTFTSELSRLNDSARLNRLLNGLV

SEQ ID NO: 72-
KAPSGRVSMIKNLQSLDPSHR

SEQ ID NO: 73-
HSDAVFTDNYTRLRKGMAVKKYLNSILN

SEQ ID NO: 74-
RPKPQQFFGLM

SEQ ID NO: 75-
APLEPVYPGDNATPENMAQYAADLRRYINMLTRPRY

SEQ ID NO: 76-
YPPKPESPGEDASPEEMNKYLTALRHYINLVTRQRY

SEQ ID NO: 77-
YPSKPDNPGEDAPAEDMARYYSALRHYINLITRQRY

SEQ ID NO: 78-
HSQGTFTSDYSKYLDSRRAQDFVQWLMNT

SEQ ID NO: 79-
DRVYIHPF

SEQ ID NO: 80-
FVPYNPPRPGQSKPFPSFPGHGPFNPKIQWPYPLPNPPGH

SEQ ID NO: 81-
GNRPVYIPPPRPPHPRL

SEQ ID NO: 82-
RFRPPIRRPPIRPPFYPPFRPPIRPPIFPPIRPPFRPPLGPFPGRR

SEQ ID NO: 83-
ALSYREAVLRAVDRINERSSEANLYRLLELDPPPKDVEDRGARKPTSFTVKETVCPRTSPQPPEQCD

SEQ ID NO: 84-
MKFTIVFLLLACVFAMAVATPGKPRPYSPRPTSHPRPIRVRREALAIEDHLAQAAIRPPPILPA

SEQ ID NO: 85-
AFPPPNVPGPRFPPPNFPGPRFPPPNFPGPRFPPPNFPGPRFPPPNFPGPPFPPPIFPGPWFPPPPPFRPPPFGPPRFP

SEQ ID NO: 86-
CYCRIPACLAGERRYGTCFLGRVWAFCC

SEQ ID NO: 87-
DHYNCVSSGGQCLYSACPIFTKIQGTCYRGKAKCCK

SEQ ID NO: 88-
RGGRLCYCRR RFCVCVGR

SEQ ID NO: 89-
DCLSGRYKGPCAVWDNETCRRVCKEEGRSSGHCSPSLKCWCEGC

SEQ ID NO: 90-
DEDMDE

SEQ ID NO: 91-
ALWKTMLKKLGTMALHAGKAALGAAADTISQGTQ

SEQ ID NO: 92-
GIGALSAKGALKGLAKGLAZHFAN

SEQ ID NO: 93-
WKPFKKIEKAVRRVRDGVAKAGPAVAVVGQAT

SEQ ID NO: 94-
GIFSKLGRKKIKNLLISGLKNVGKEVGMDVVRTGIDIAGCKIKGEC

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

EXPERIMENTAL

Figure 1B:
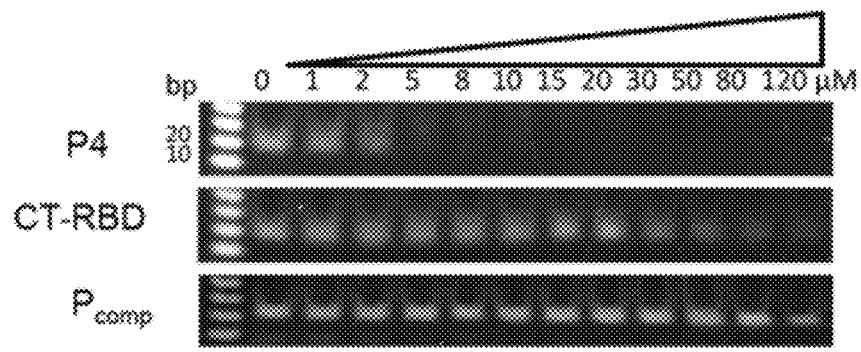
Figure 1B:
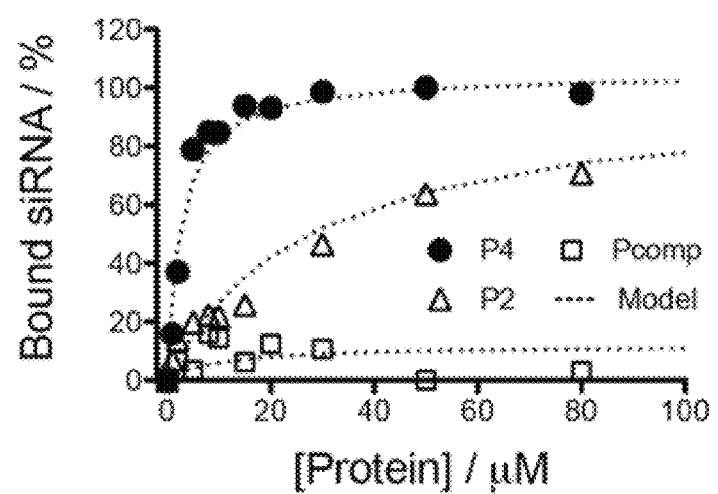
Figures 1C, 1D, 1E, 1F:
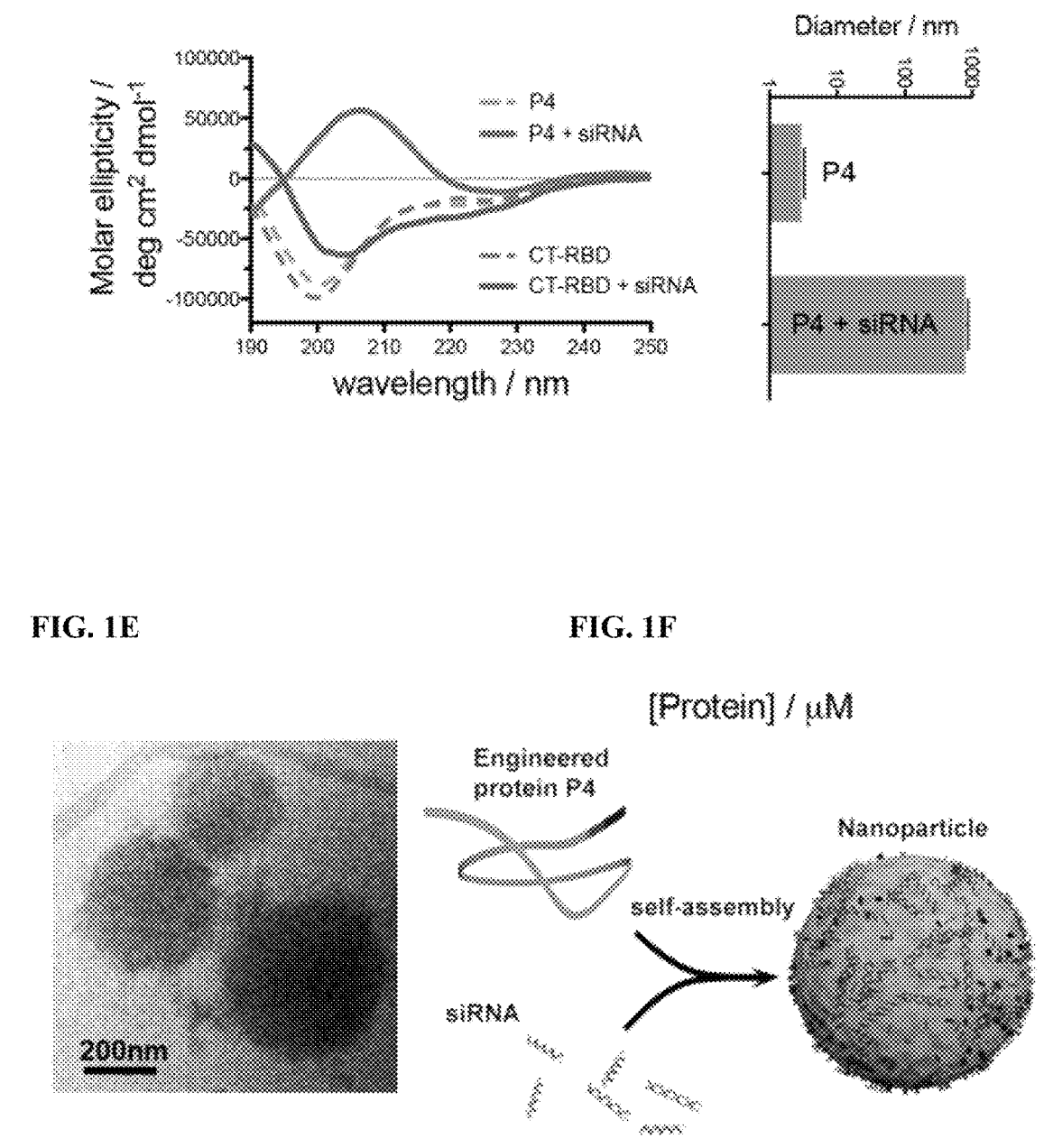
Figure 1G:
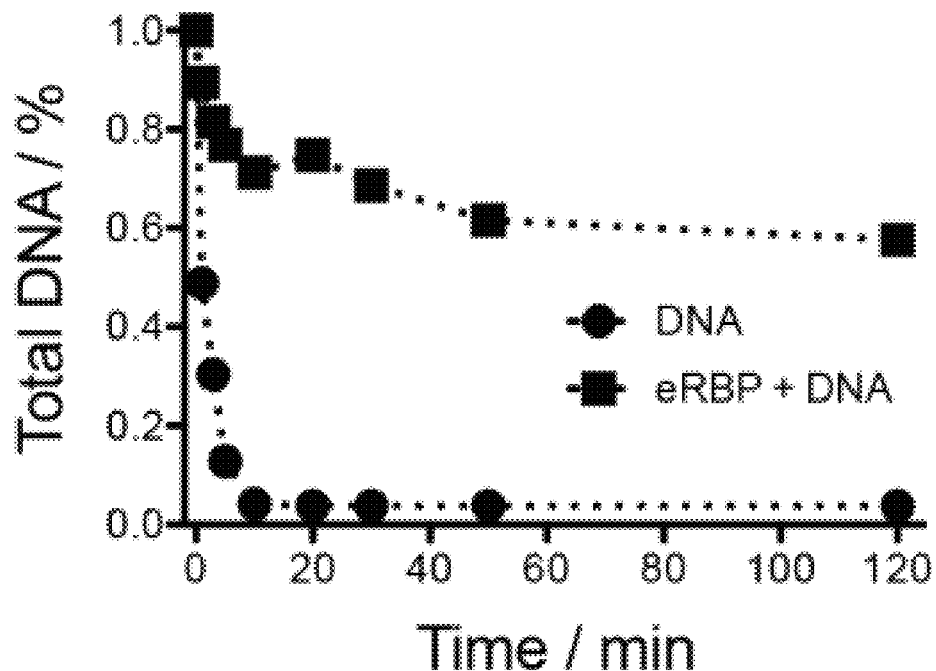
Figure 1H:
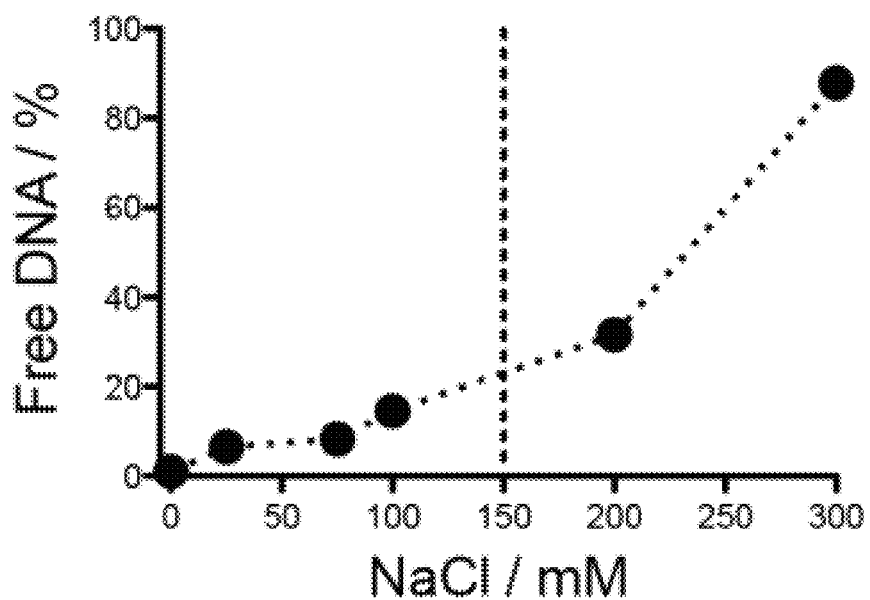
Figure 1I:
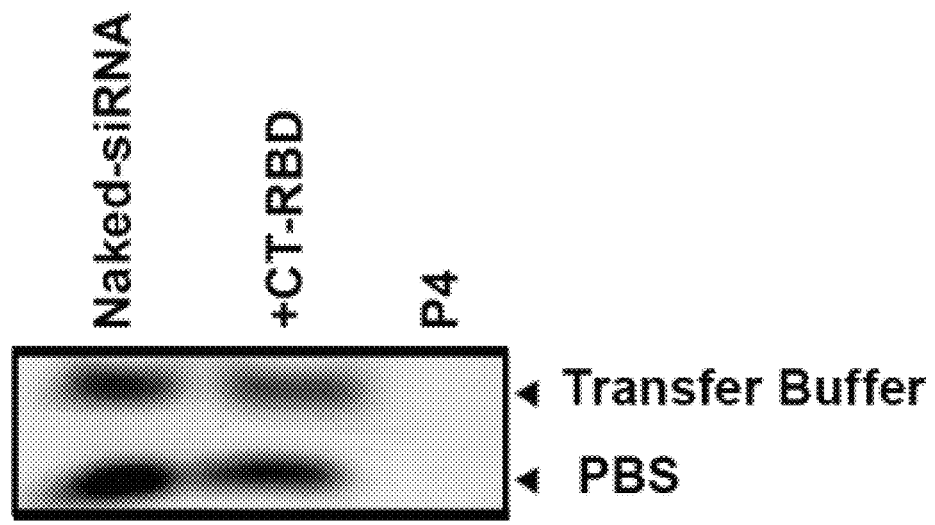
Figure 2C:
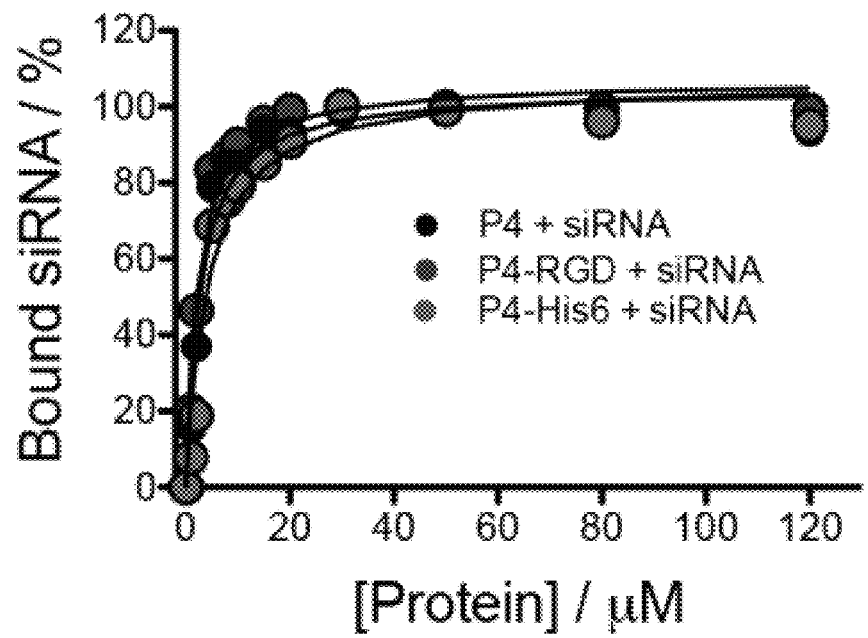
Figure 2D:
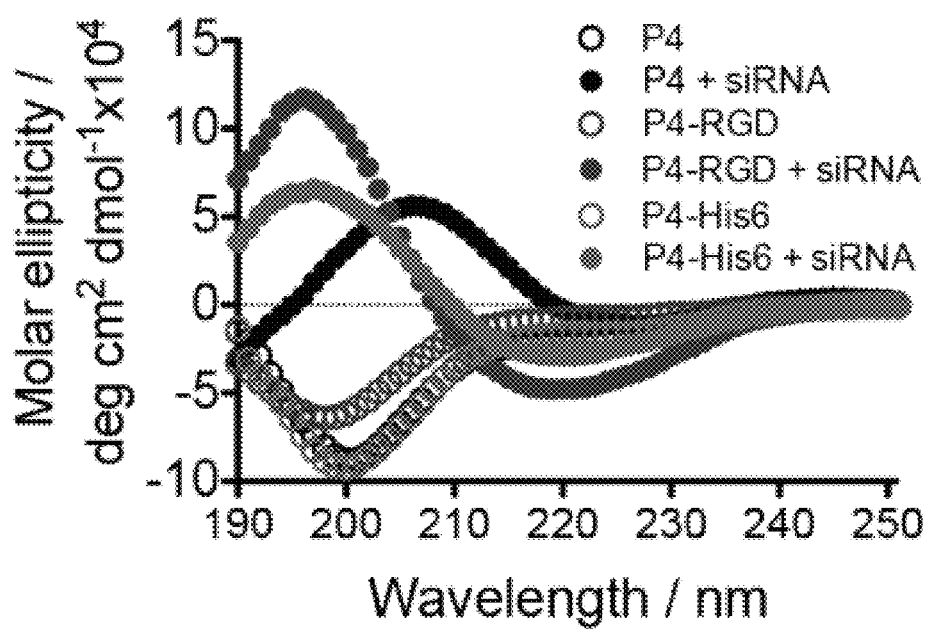
Figure 2E:
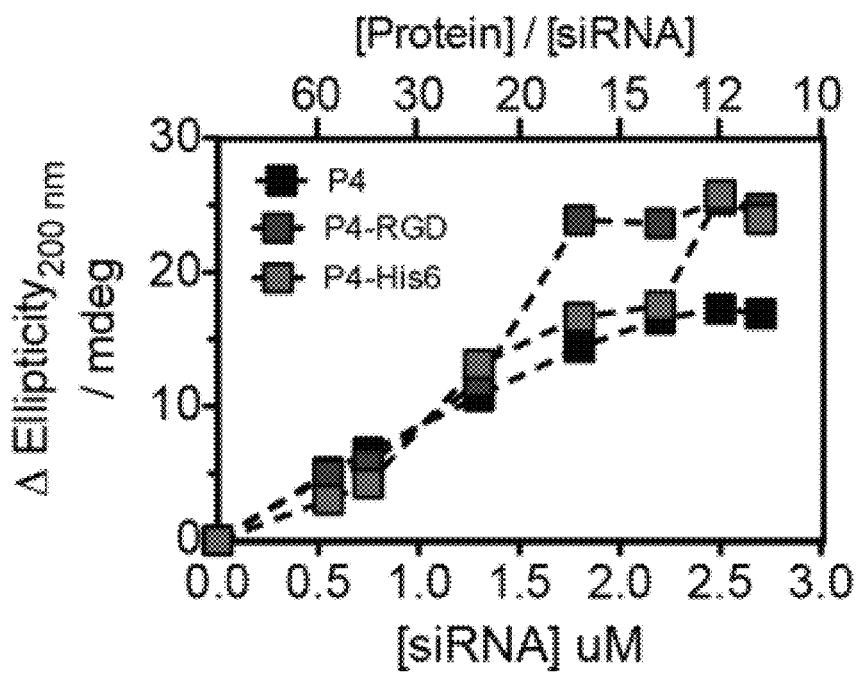
Figure 2F:
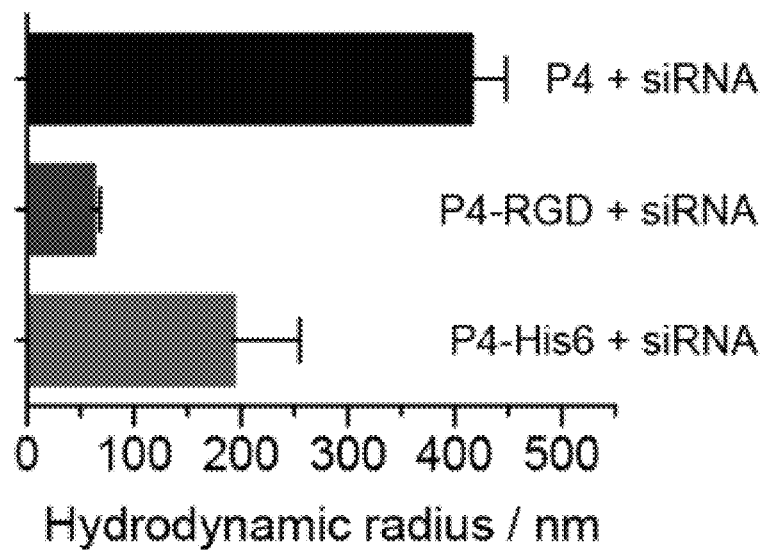
Figure 2G:
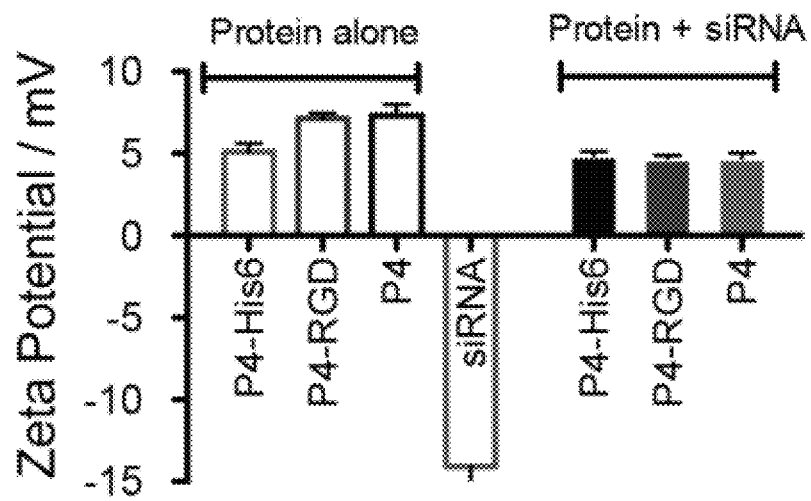
Figure 2H:
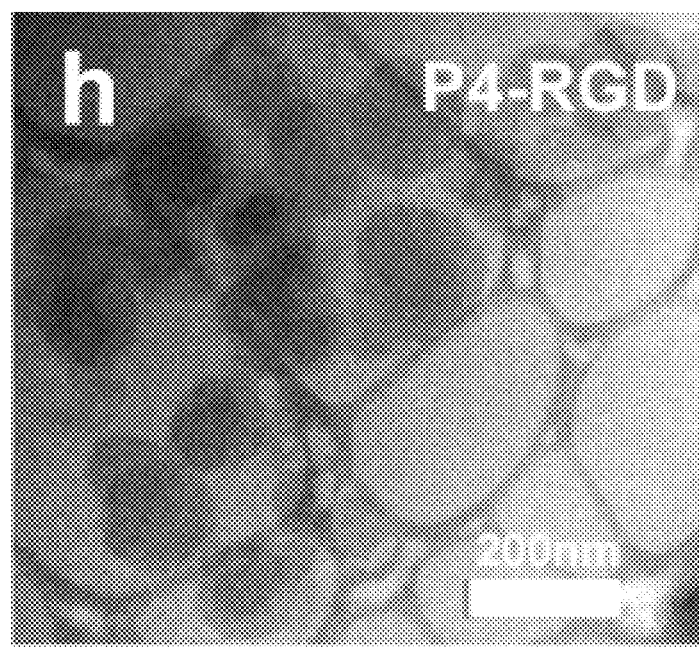
Figure 2I:
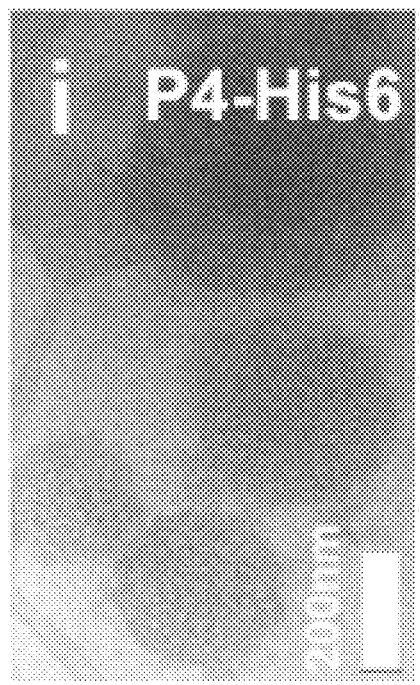
Figure 2J:
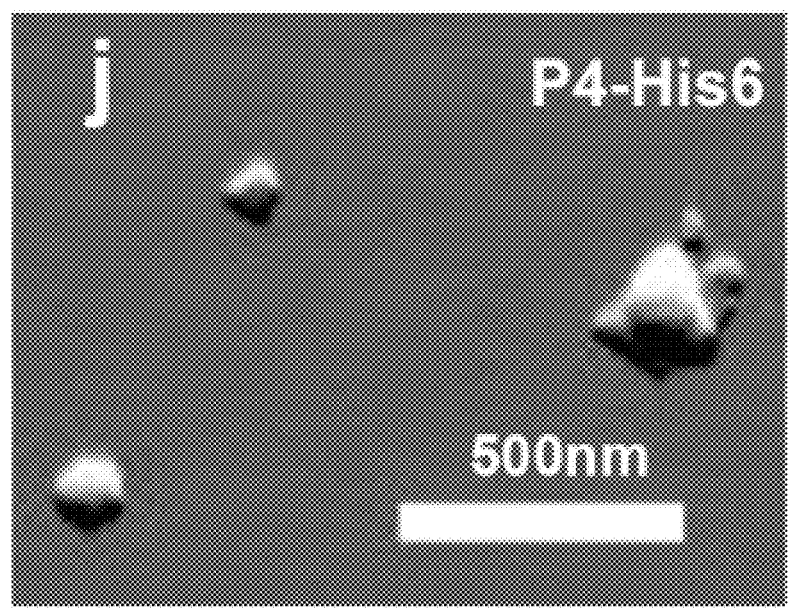
Figure 3A:
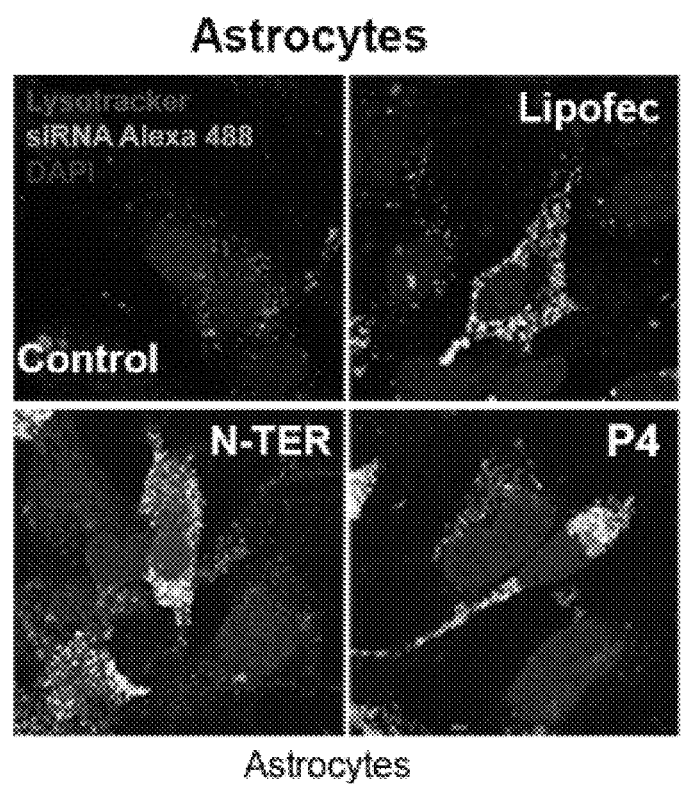
FIGS. 3A-M. siRNA internalization and gene knockdown by P4 nanoparticles and toxicity in primary neural cells. Confocal images of glial cells (A) and neurons (E) stained with lysotracker (endosomes), siRNAAlexa488 molecules and DAPI (nucleus). Cell survival after incubation with different trasnfectants including P4 for glial (B) and for neurons (F). Green Flow cytometry histograms of internalized fluorescently labeled siRNA-Alexa488 into primary cortical astrocytes (C) and primary cortical neuron (G) after 24 h. Percentage of positive cells that internalized carried fluorescently labeled siRNAAlexa488 (top) and Fluorescence increment in cells transfected with siRNAalexa488 (bottom) in primary cortical astrocytes (D) and neurons (H). Confocal images of glial cells stained with GFAP (I) and neurons stained with Tuj-1 and Synaptophysin (K) after 24 h of transfection. Western blots and densitometry (intensity values normalized to actin) showed the expression of GFAP marker in glial cell cultures (J) and Tuj-1 and synaptophysin in neuronal cultures (l) after 24 h of transfection in control condition (C), P4 alone (P4), P4 nanoparticle with negative siRNA (P4 (−)) and P4 nanoparticle with siRNA GFAP/Synaptophysin (P4(+)). (m) Blocking internalization of siRNAAlexa488-P4 nanoparticles with endocytosis chemical inhibitors: Filipin (caveolae-endocytosis), Amiloride (macropinocytosis) and chlorpromazine (clathrin-mediated endocytosis) (left astrocytes, right neurons). *$P<0.05$, **$P<0.001$, LSD test (compared with Control), #$P<0.05$, ##$P<0.001$, LSD test (compared with siRNA), n=3.
Figure 3B:
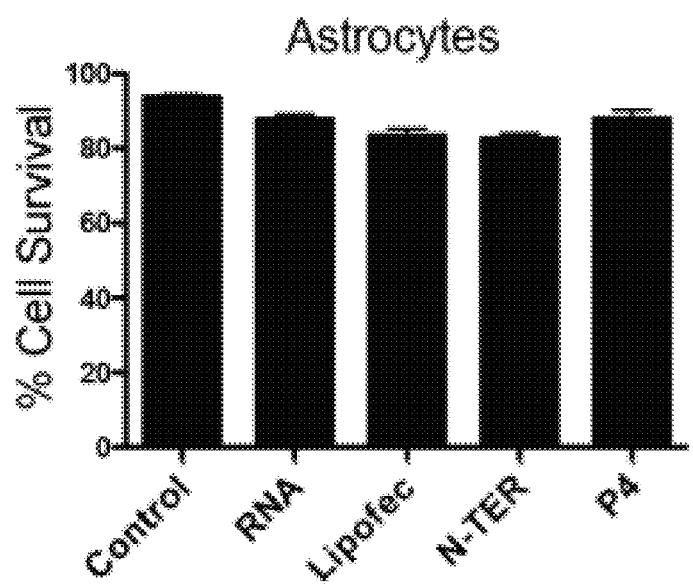
Figure 3C:
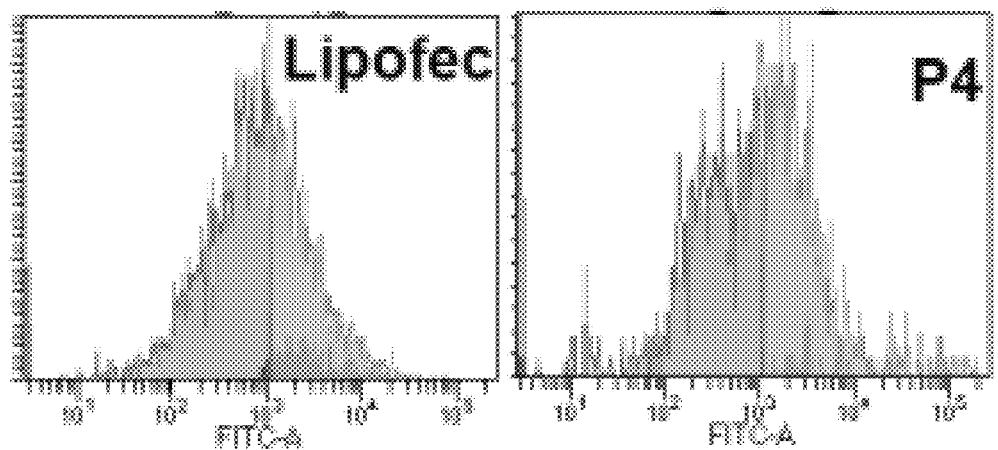
Figure 3D:
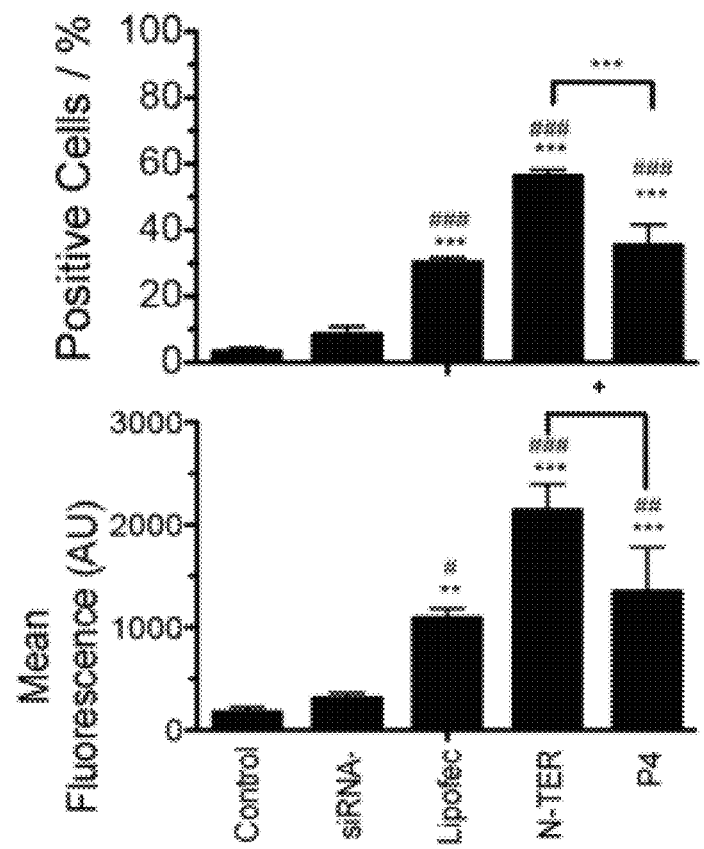
Figure 3E:
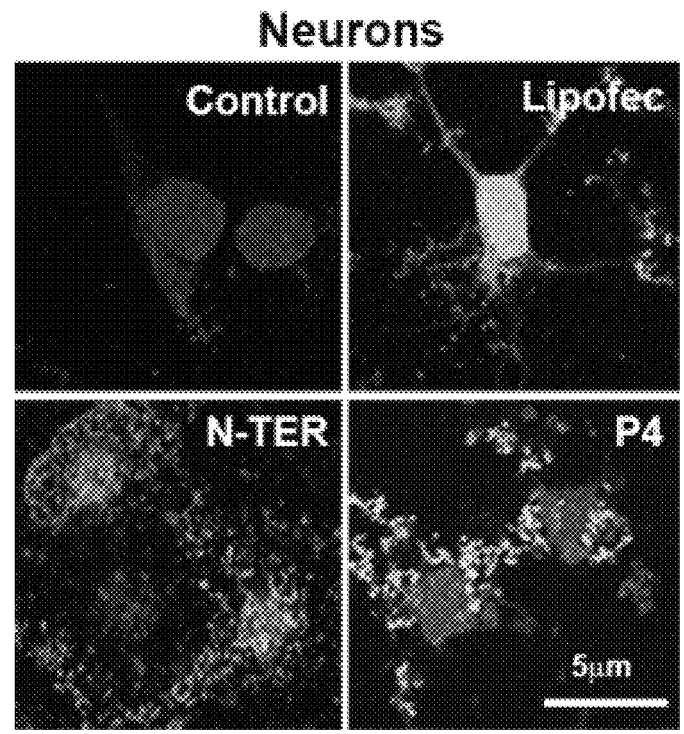
Figure 3F:
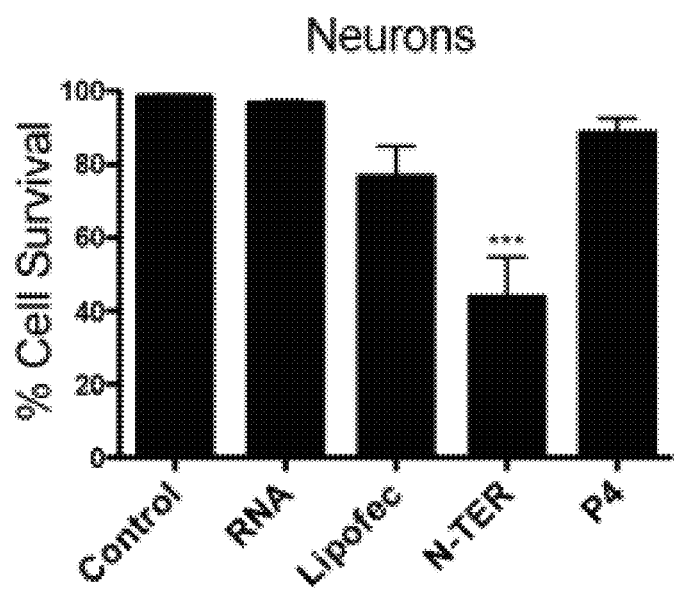
Figure 3G:
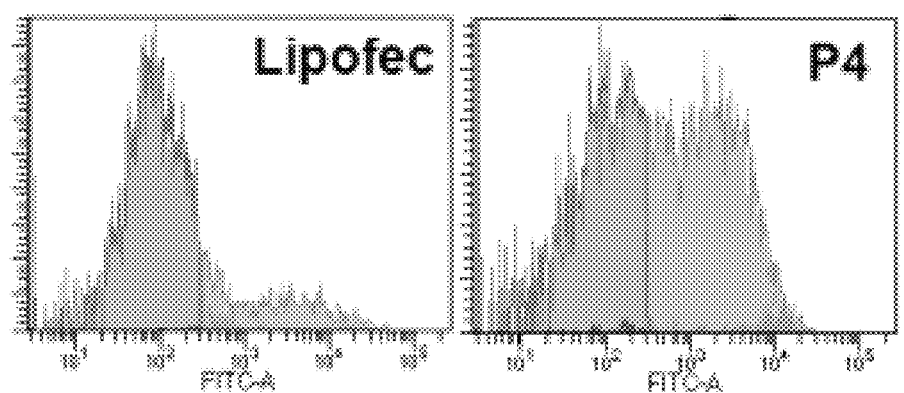
Figure 3H:
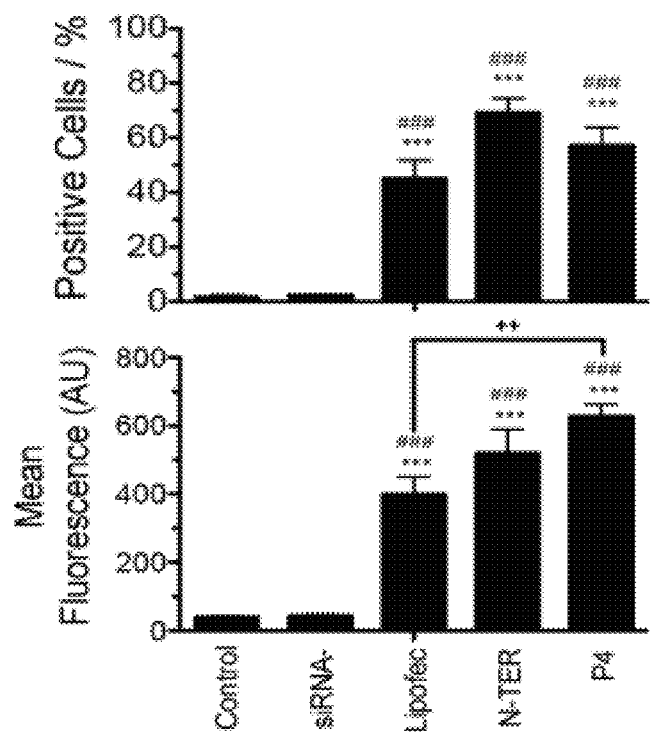
Figure 3I:
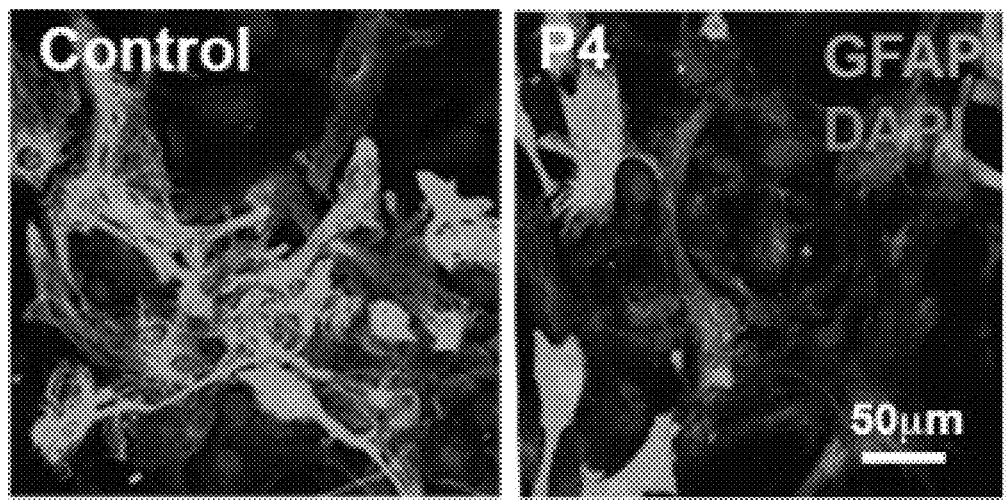
Figure 3J:
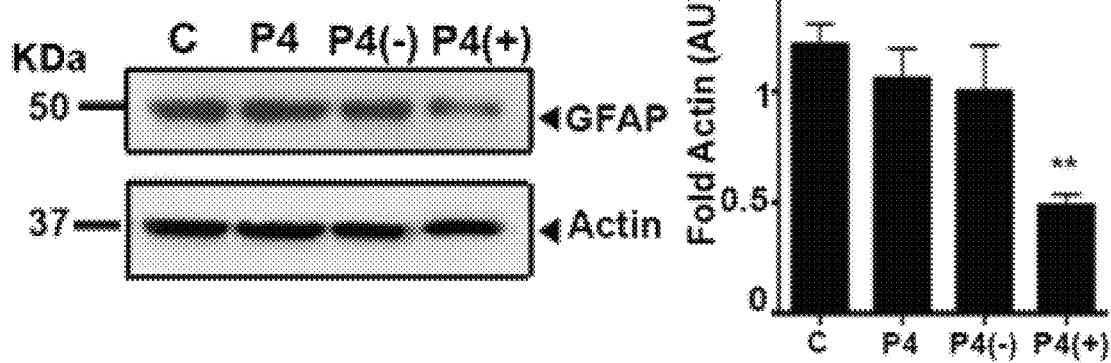
Figure 3K:
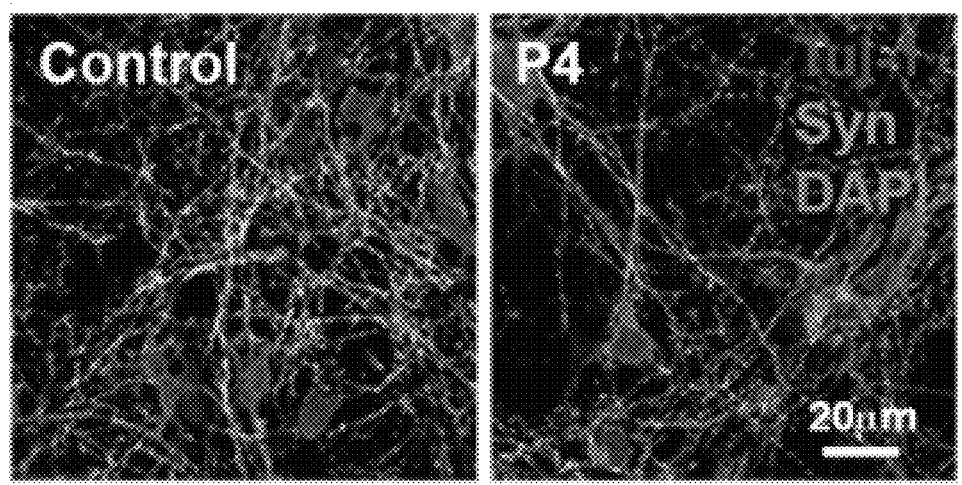
Figure 3L:
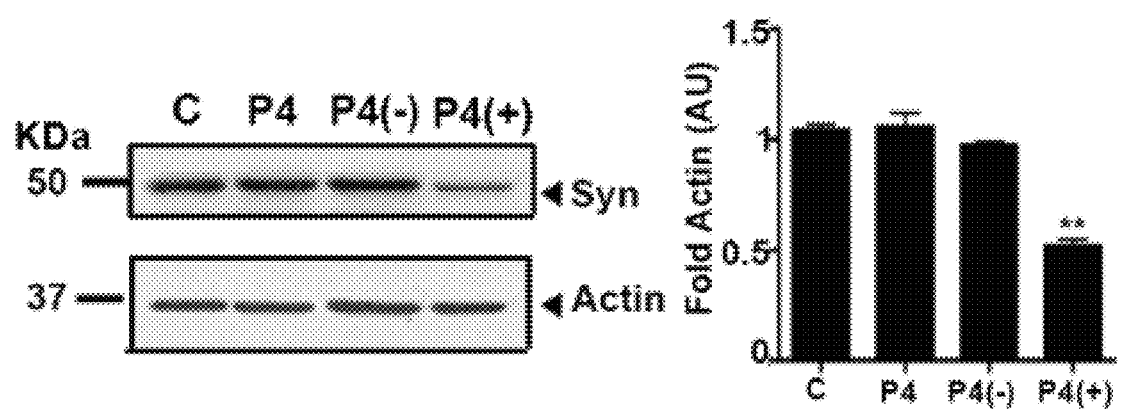
Figure 3M:
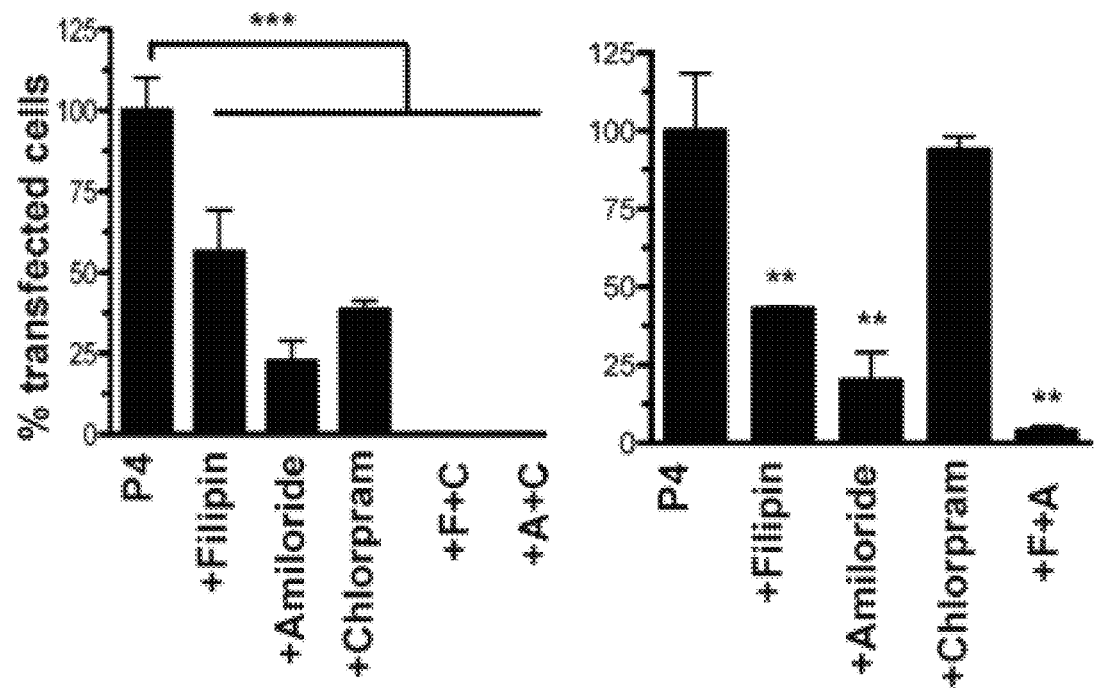
Figure 4A:
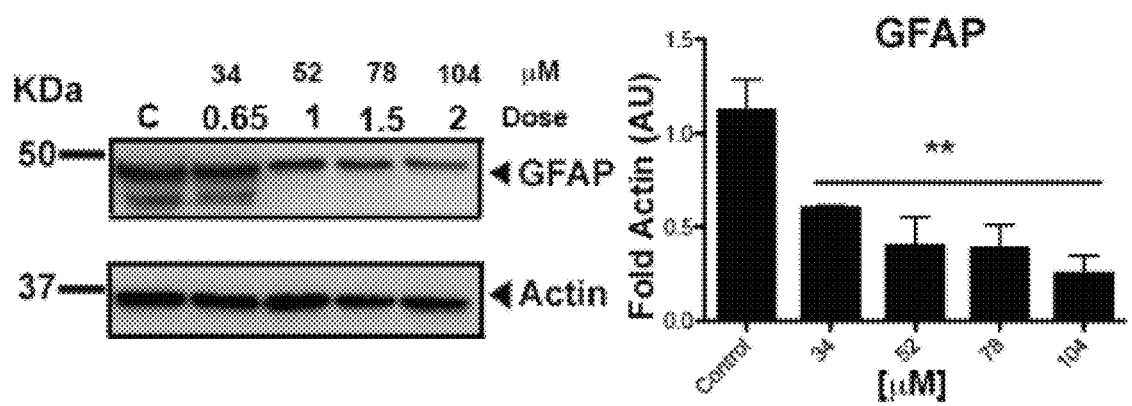
FIGS. 4A-H. Dose-response and time-response curves of gene knockdown by P4 nanoparticles and associated toxicity. Dose-response of siRNA-mediated gene knockdown in glial cells (A) and neurons (C) and their toxicity levels (B & D) for glial and neuron cells, respectively. Time-response of siRNA-mediated gene knockdown in glial cells (E) and neurons (G); and their toxicity levels (F & H) for glial and neuron cells, respectively. *$P<0.05$, **$P<0.001$, LSD test (compared with Control/neg. siRNA Control), #$P<0.05$, ##$P<0.001$, LSD test (compared with other conditions), n=3.
Figure 4B:
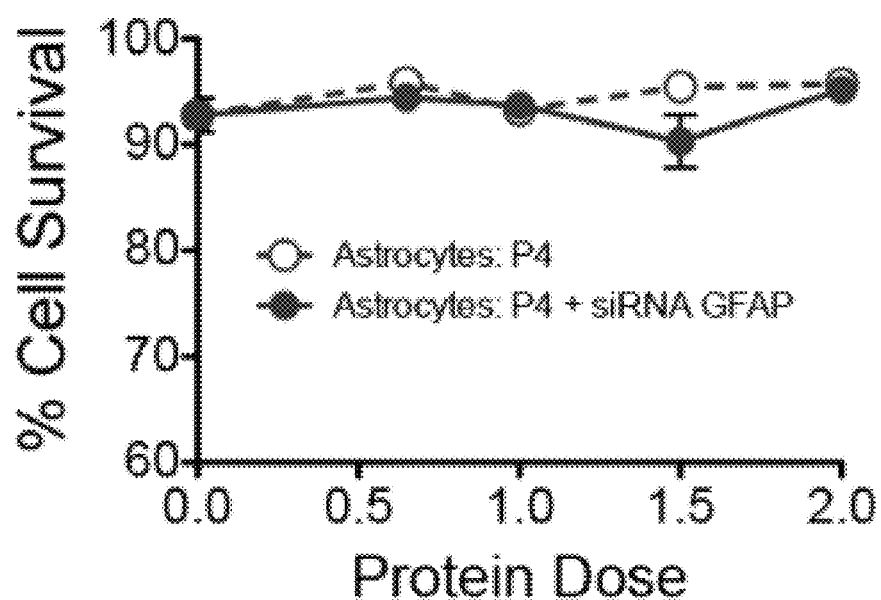
Figure 4C:
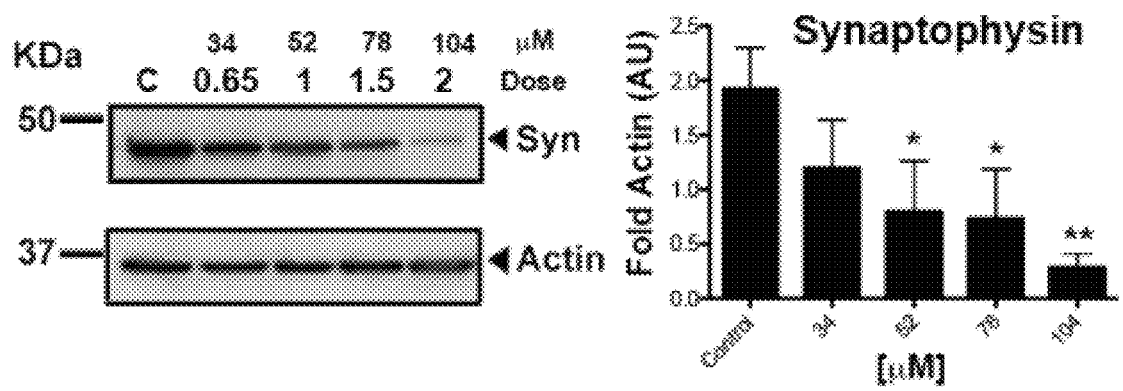
Figure 4D:
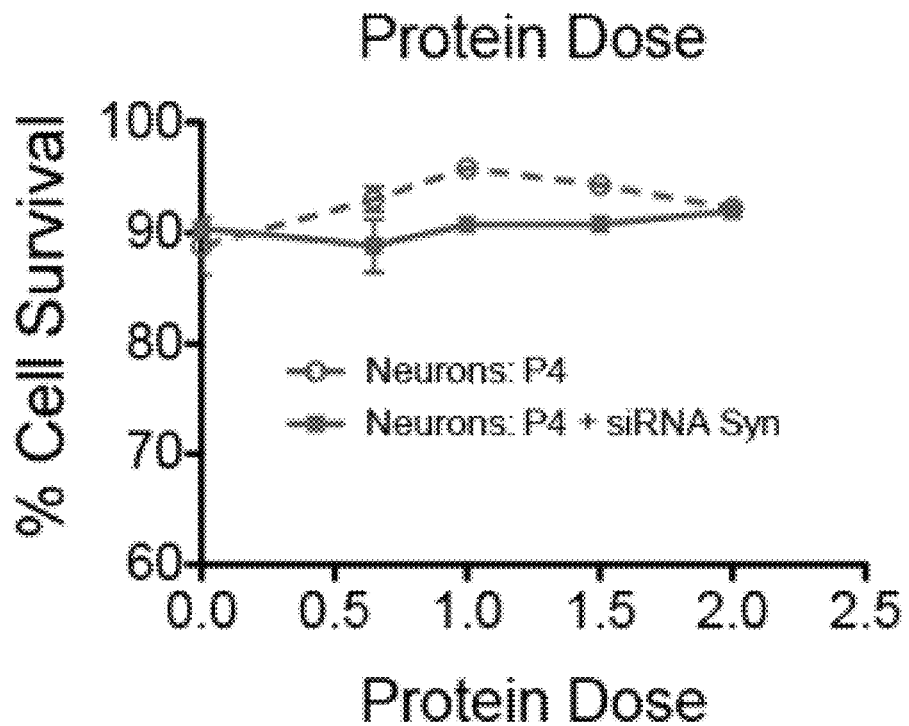
Figure 4E:
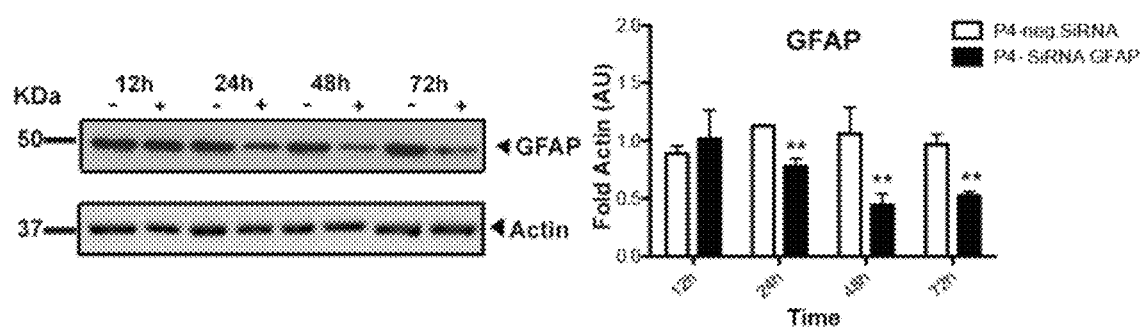
Figure 4F:
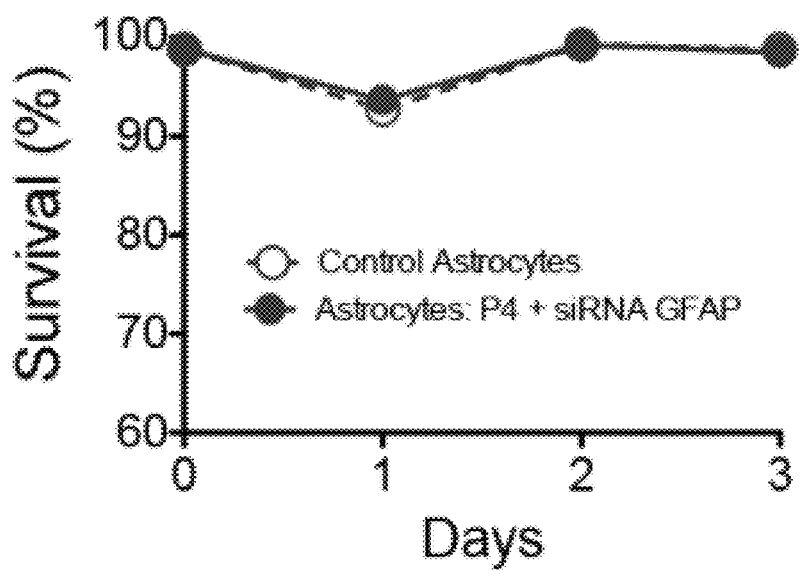
Figure 4G:
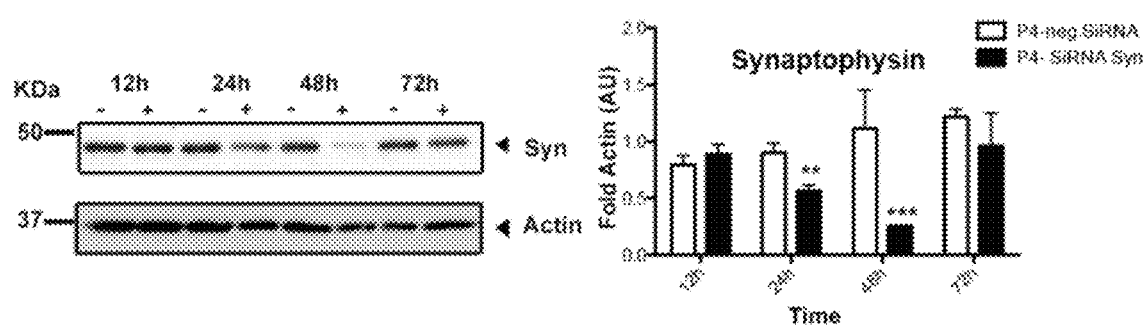
Figure 4H:
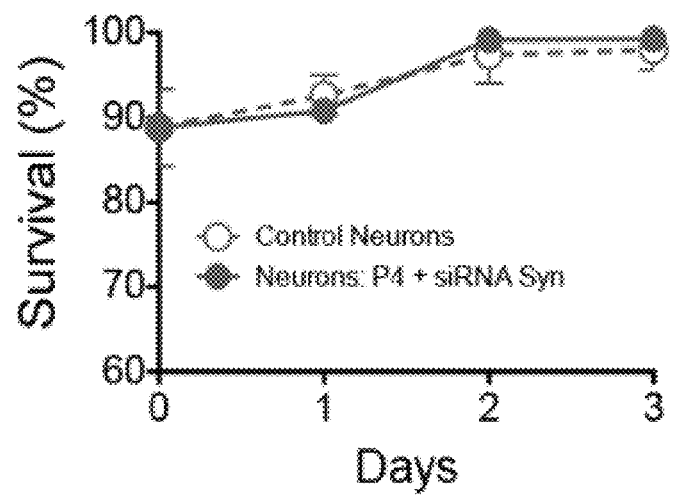
Figure 5A:
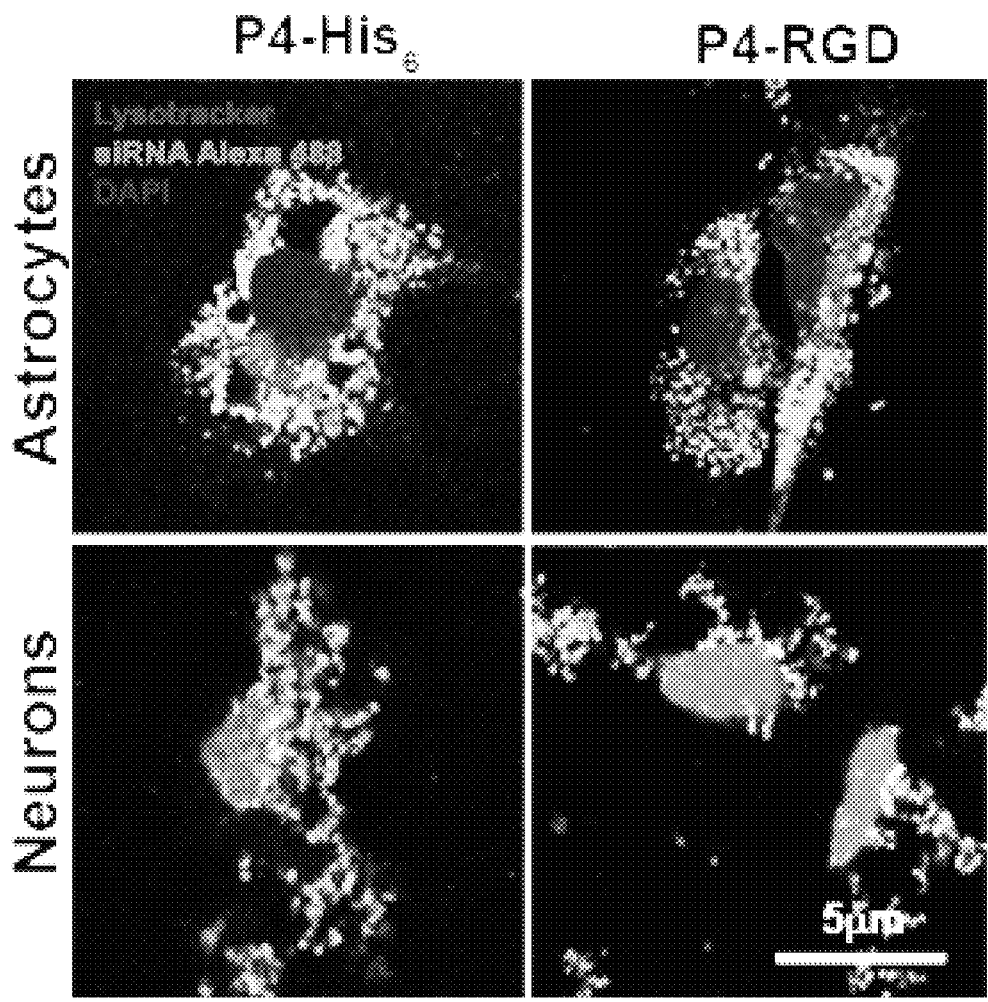
FIGS. 5A-O. siRNA internalization and gene knockdown by functionalized P4 nanoparticles and toxicity. (A) Confocal images of glial cells (top) and neurons (bottom) stained with lysotracker (endosomes), siRNAAlexa488 molecules and DAPI (nucleus). (B, E) % of positive cells that internalized carried fluorescently labeled siRNAAlexa488 (top) and Fluorescence increment in cells transfected with siRNAalexa488 (bottom) in primary cortical astrocytes (B) and neurons (E). (C, F) Co-localization of green siRNAAlexa488 in endosomes labeled with lysotracker in glial cells (C) and neurons (F). (D,G) Cell survival after incubation with P4 nanoparticles in astroglial cells (D) and neuronal primary culture (G). (H,K) Confocal images of glial cells stained with GFAP (H) and neurons stained with Tuj-1 and Synaptophysin (K) after 24 h of transfection. (I, L) Western blots showed the expression of GFAP marker in glial cell cultures (I) and Tuj-1 and synaptophysin in neuronal cultures (L) after 24 h of transfection with P4 nanoparticles carrying a siRNA molecule. (J, M) Western blot densitometry (intensity values normalized to actin). (N) Firing rate of primary neuronal cultures transfected with P4 nanoparticles carrying the siRNA-Synaptophysin. (O) Scheme of proposed mechanism of action, P4-siRNA nanoparticles are internalized and after endosome escape the siRNA forms the RISC complex knocking down the expression of the targeted protein. *$P<0.05$, **$P<0.001$, LSD test (compared with Control/neg. siRNA Control), #$P<0.05$, ##$P<0.001$, LSD test (compared with other conditions), n=3.
Figure 5B:
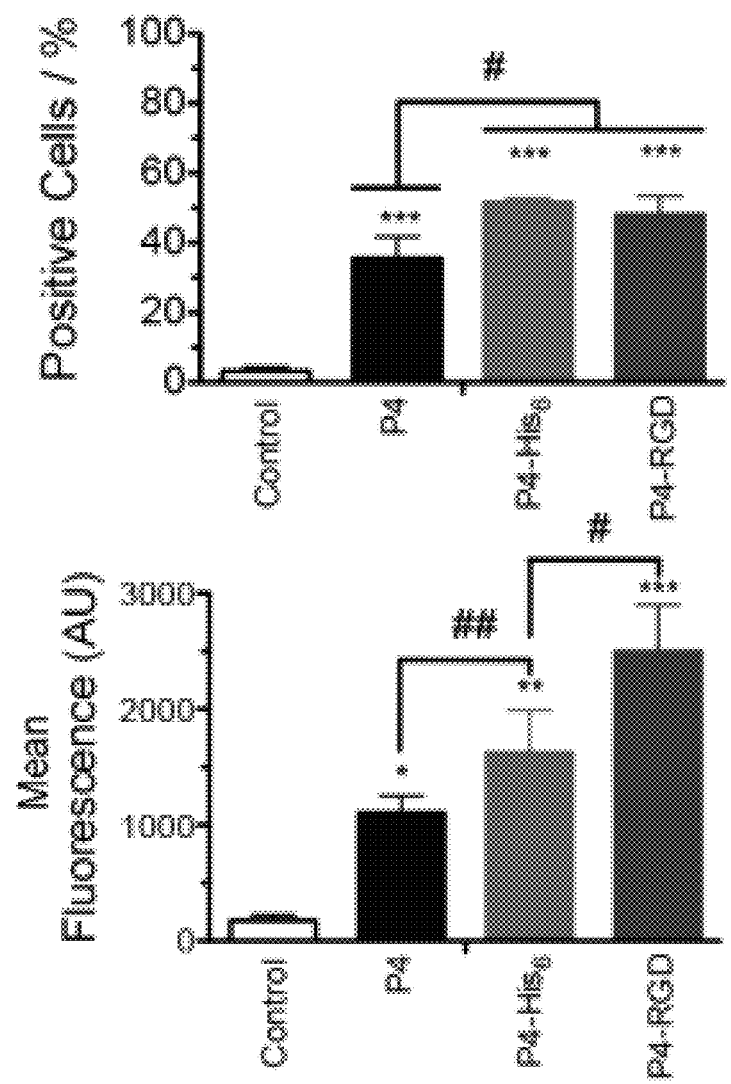
Figure 5C:
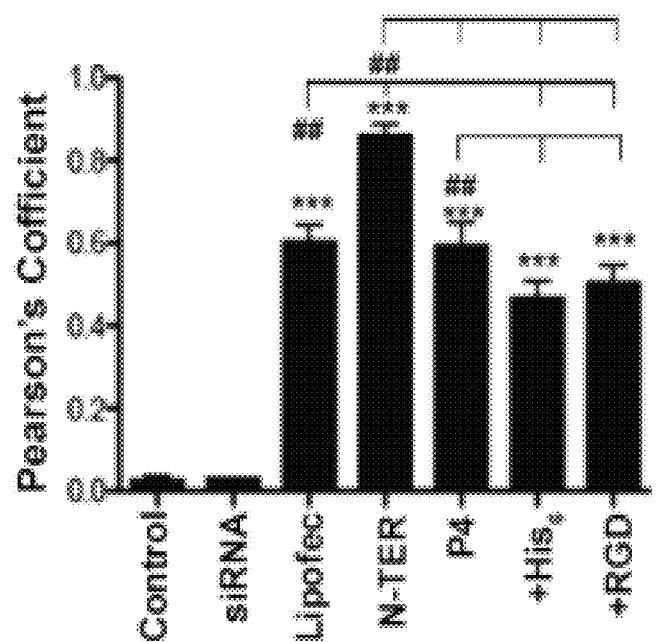
Figure 5D:
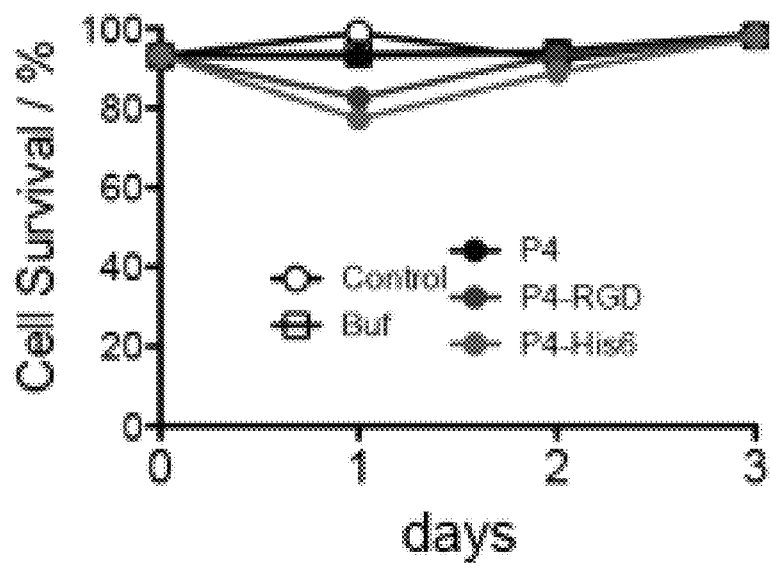
Figure 5E:
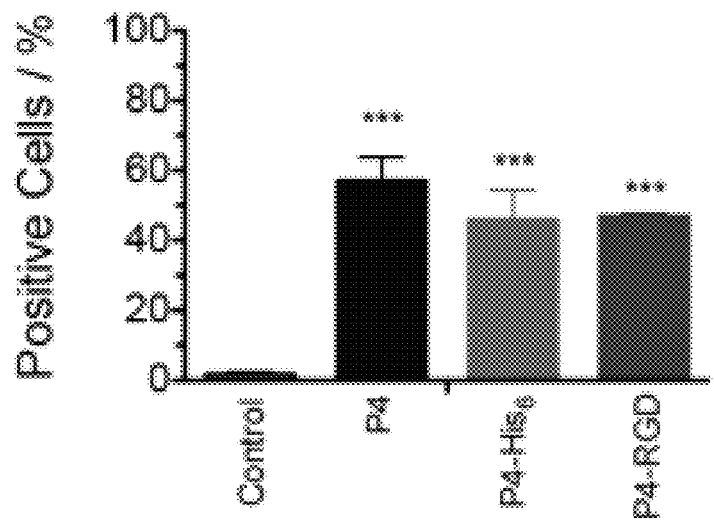
Figure 5F:
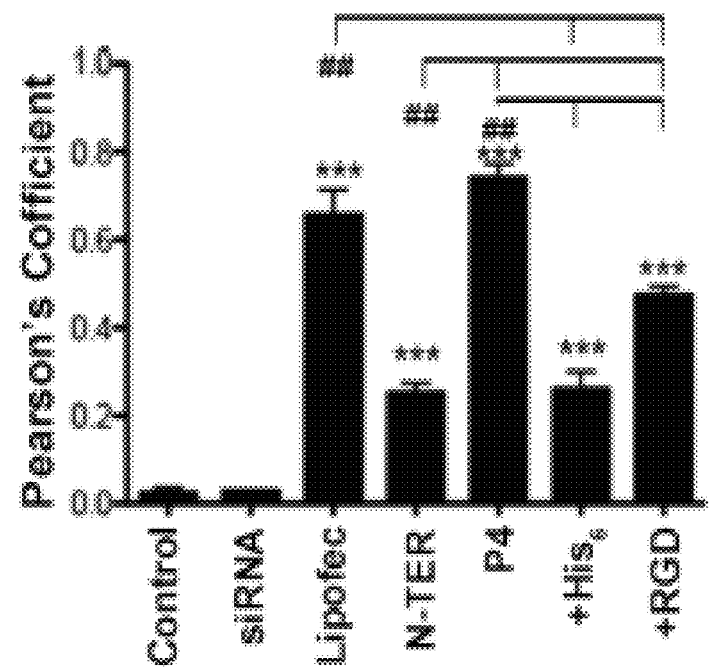
Figure 5G:
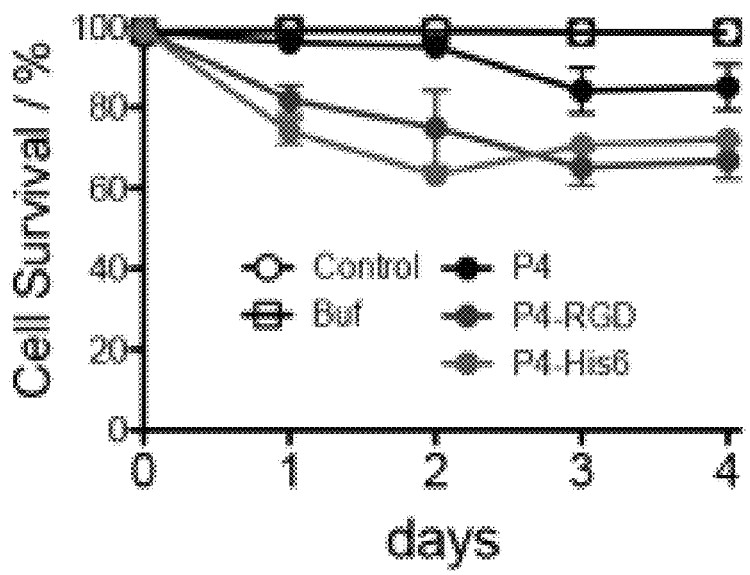
Figure 5H:
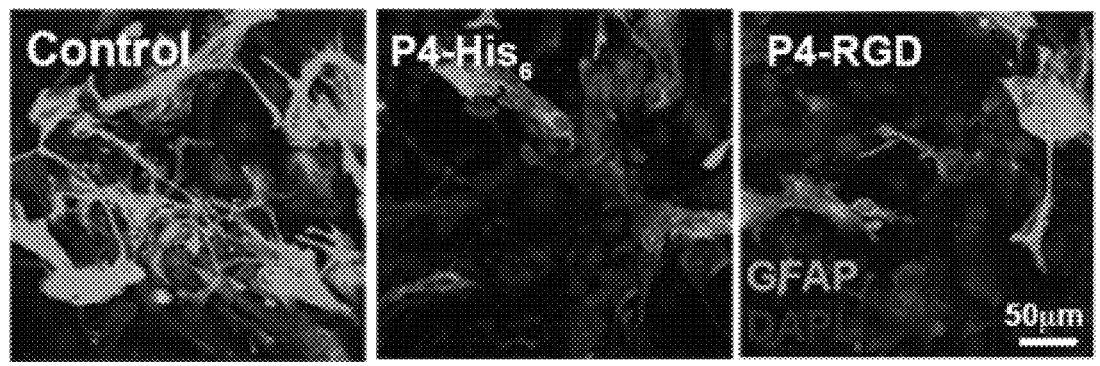
Figure 5I:
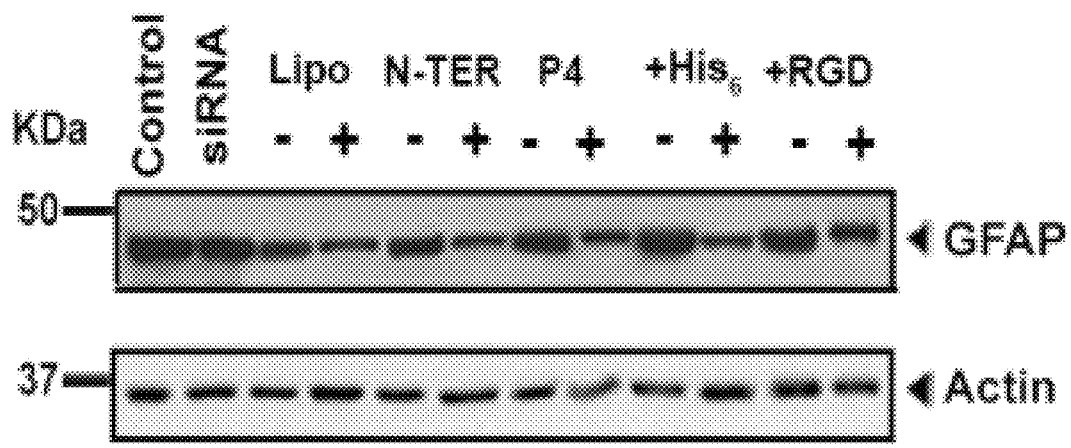
Figure 5J:
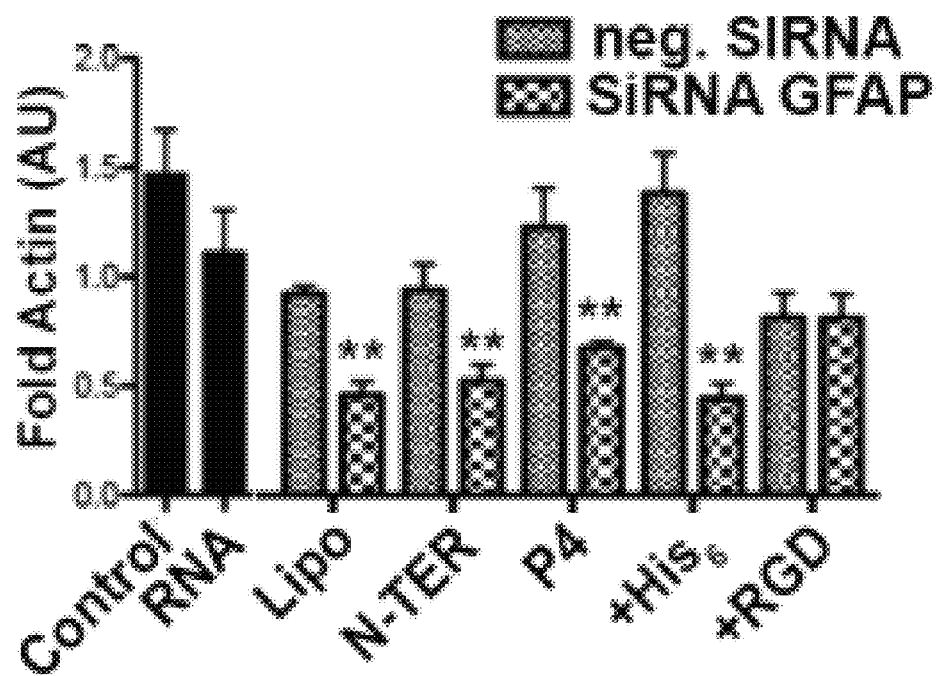
Figure 5K:
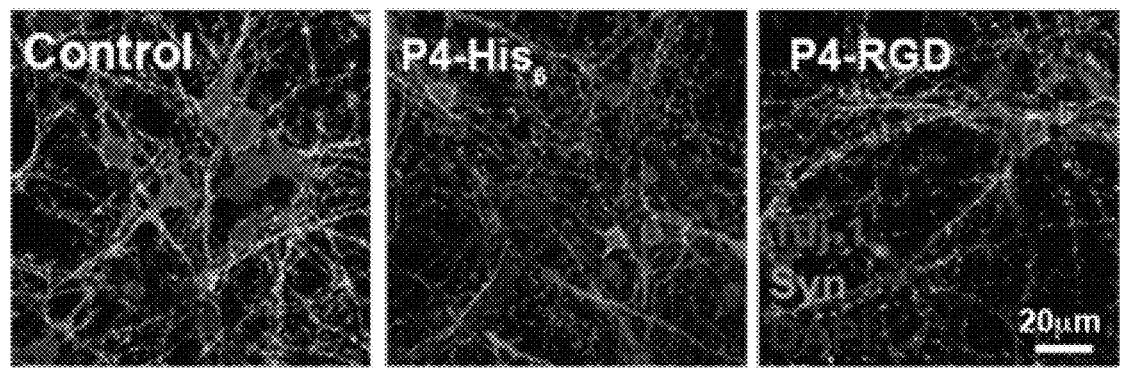
Figure 5L:
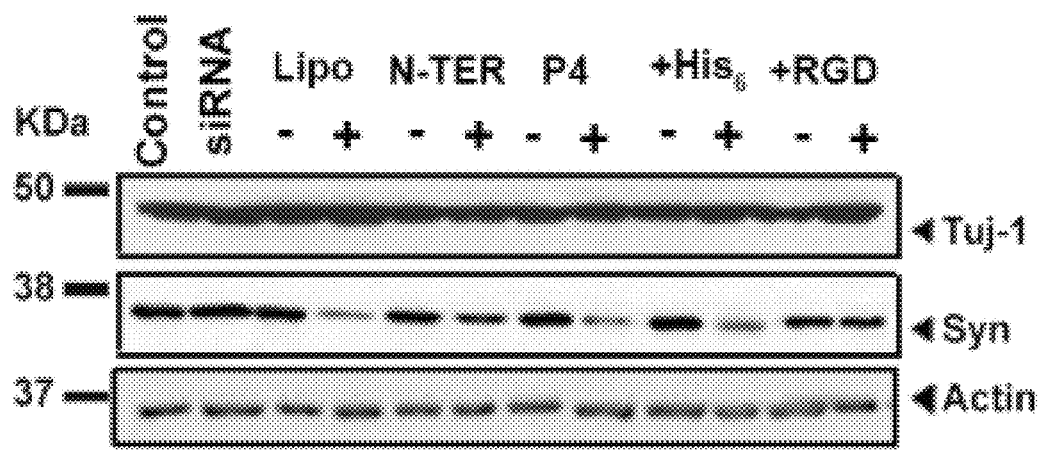
Figure 5M:
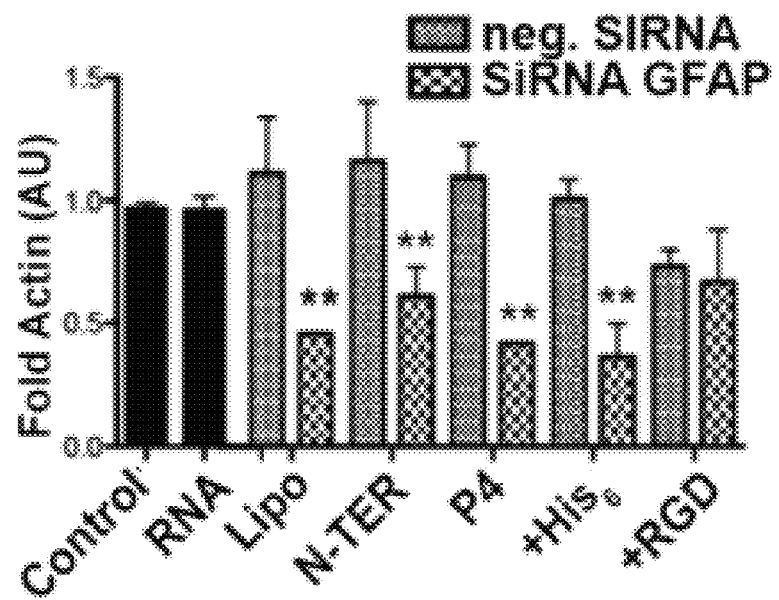
Figure 5N:
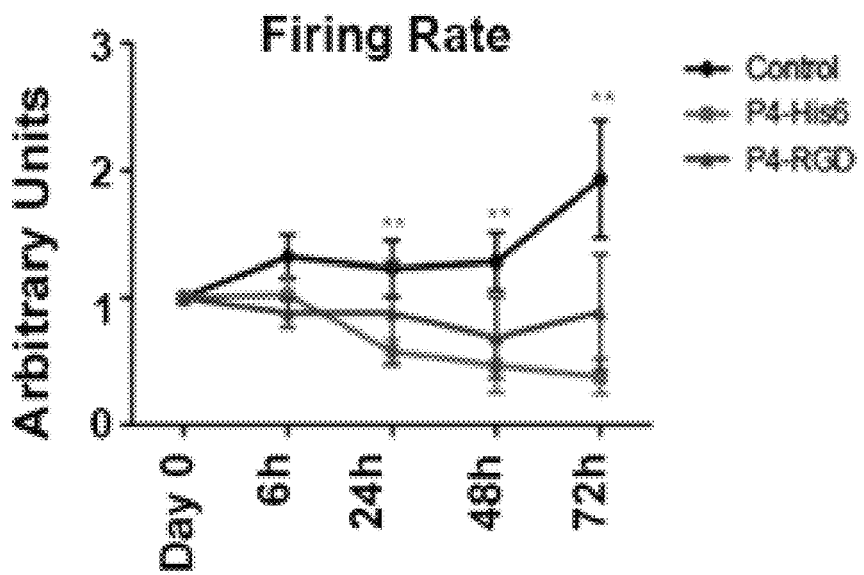
Figure 5O:
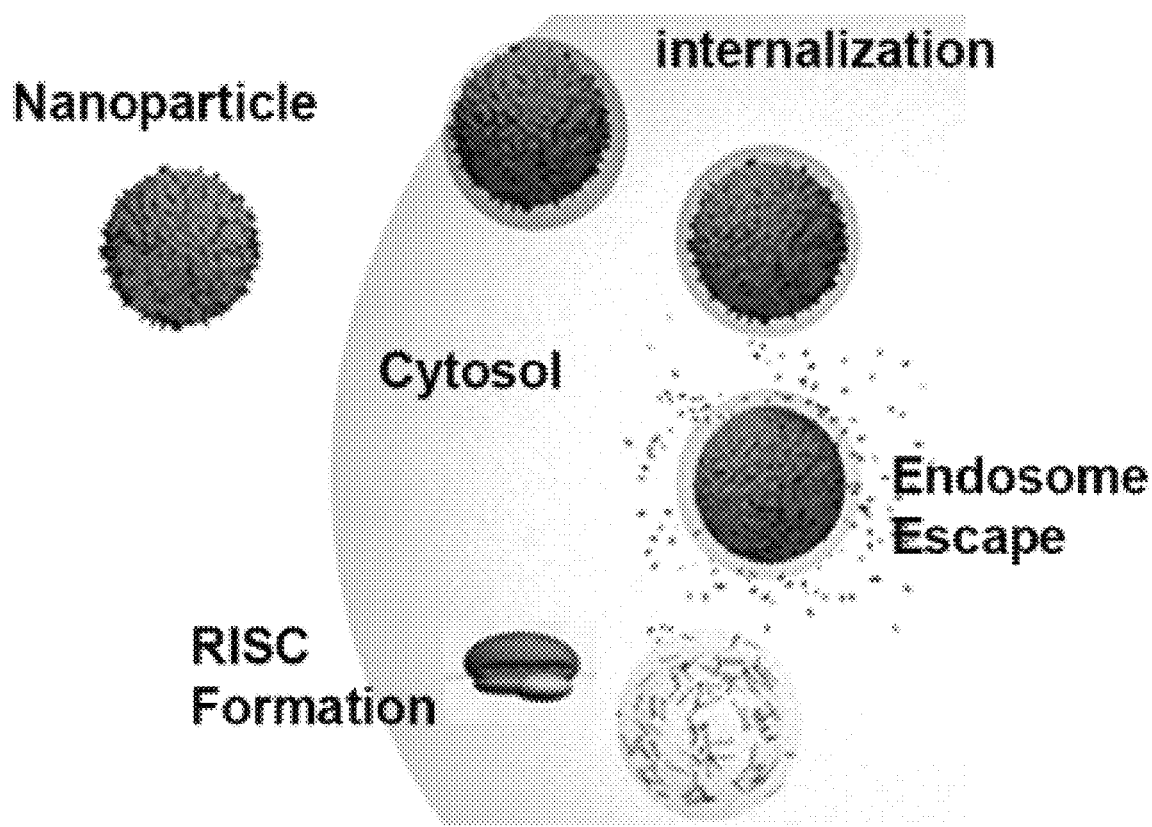

Experiments conducted during development of embodiments herein demonstrate the self-assembly of nanoparticles from complexes of cargo nucleic acids (e.g., siRNA) and polypeptides within the scope described herein (e.g., comprising linked NABD and AD). Experiments further demonstrate the delivery of such cargo nucleic acids to cells by P/NA nanoparticles, release of nanoparticles and cargo nucleic acid from endosomes, and function (e.g., gene knockdown) of the cargo nucleic acids within the cells. Experiments additionally demonstrate the functionality of polypeptides within the scope described herein (e.g., comprising linked NABD and AD) having bioactive peptides fused thereto. Experiments demonstrating the above and other testing of exemplary polypeptides and nanoparticles are described in the Brief Description of the Drawings and the results of such exemplary experiments are depicted in FIGS. 1-5.

The invention claimed is:

1. A polypeptide comprising an assembly domain and a nucleic-acid-binding domain (NABD),
   wherein the assembly domain comprises an amino acid sequence selected from the group consisting of: SEQ ID NO:2 and SEQ ID NO:12; and
   wherein upon binding of the NABD to a nucleic acid to form a polypeptide/nucleic acid complex, the assembly domain facilitates self-assembly of the polypeptide/nucleic acid complex into nanoparticles.

2. The polypeptide of claim 1, wherein the amino acid sequence comprises SEQ ID NO:2.

3. The polypeptide of claim 2, wherein the amino acid sequence comprises SEQ ID NO:1.

4. The polypeptide of claim 2, wherein the amino acid sequence comprises SEQ ID NO:5.

5. The polypeptide of claim 1, wherein the amino acid sequence comprises SEQ ID NO:12.

6. The polypeptide of claim 5, wherein the amino acid sequence comprises SEQ ID NO:11.

7. The polypeptide of claim 1, wherein the NABD binds single-stranded (ss) and/or double-stranded DNA and/or RNA.

8. The polypeptide of claim 1, wherein the NABD and assembly domain are connected by a linker moiety.

9. The polypeptide of claim 1, further comprising a bioactive domain that enhances one or more characteristics selected from the group consisting of cell internalization, cell-targeting, endosome escape, and nuclear delivery.

10. The polypeptide of claim 9, wherein the bioactive domain is selected from the group consisting of SEQ ID NO: 6, SEQ ID NO: 8, and SEQ ID NO: 10.

11. A carrier nanoparticle comprising: (a) cargo nucleic acids, and (b) polypeptides of claim 1.

12. The carrier nanoparticle of claim 11, wherein the cargo nucleic acid is a single stranded or double stranded DNA or RNA.

13. The carrier nanoparticle of claim 11, wherein binding of the polypeptide to the cargo nucleic acid facilitates self-assembly of the polypeptide/nucleic acid complexes into the carrier nanoparticles.

14. The carrier nanoparticle of claim 11, wherein the nanoparticle is between 20 and 800 nm in diameter.

15. A method of delivering a cargo nucleic acid into a cell, comprising exposing the cell to a nanoparticle of claim 11.

* * * * *

SEQUENCE LISTING

<160> NUMBER OF SEQ ID NOS: 95

<210> SEQ ID NO 1
<211> LENGTH: 47
<212> TYPE: PRT
<213> ORGANISM: Artificial sequence
<220> FEATURE:
<223> OTHER INFORMATION: Synthetic peptide

<400> SEQUENCE: 1

Ser Ile Arg Lys Leu Glu Tyr Glu Ile Glu Glu Leu Arg Leu Arg Ile
1               5                   10                  15

Gly Gly Gly Thr Phe Val Glu Thr Gly Ser Gly Thr Ser Lys Gln Val
            20                  25                  30

Ala Lys Arg Val Ala Ala Glu Lys Leu Leu Thr Lys Phe Lys Thr
        35                  40                  45

<210> SEQ ID NO 2
<211> LENGTH: 17
<212> TYPE: PRT
<213> ORGANISM: Artificial sequence
<220> FEATURE:
<223> OTHER INFORMATION: Synthetic peptide

<400> SEQUENCE: 2

Ser Ile Arg Lys Leu Glu Tyr Glu Ile Glu Glu Leu Arg Leu Arg Ile
1               5                   10                  15

Gly

<210> SEQ ID NO 3
<211> LENGTH: 28
<212> TYPE: PRT
<213> ORGANISM: Artificial sequence
<220> FEATURE:
<223> OTHER INFORMATION: Synthetic peptide

<400> SEQUENCE: 3

Thr Phe Val Glu Thr Gly Ser Gly Thr Ser Lys Gln Val Ala Lys Arg
1               5                   10                  15

Val Ala Ala Glu Lys Leu Leu Thr Lys Phe Lys Thr
            20                  25

<210> SEQ ID NO 4
<211> LENGTH: 2
<212> TYPE: PRT
<213> ORGANISM: Artificial sequence
<220> FEATURE:
<223> OTHER INFORMATION: Synthetic peptide

<400> SEQUENCE: 4

Gly Gly
1

<210> SEQ ID NO 5
<211> LENGTH: 52
<212> TYPE: PRT
<213> ORGANISM: Artificial sequence
<220> FEATURE:
<223> OTHER INFORMATION: Synthetic peptide

<400> SEQUENCE: 5

Cys Arg Gly Asp Cys Ser Ile Arg Lys Leu Glu Tyr Glu Ile Glu Glu
1               5                   10                  15

Leu Arg Leu Arg Ile Gly Gly Gly Thr Phe Val Glu Thr Gly Ser Gly
            20                  25                  30

Thr Ser Lys Gln Val Ala Lys Arg Val Ala Ala Glu Lys Leu Leu Thr
        35                  40                  45

Lys Phe Lys Thr
    50

<210> SEQ ID NO 6
<211> LENGTH: 5
<212> TYPE: PRT

```
<213> ORGANISM: Artificial sequence
<220> FEATURE:
<223> OTHER INFORMATION: Synthetic peptide

<400> SEQUENCE: 6

Cys Arg Gly Asp Cys
1               5

<210> SEQ ID NO 7
<211> LENGTH: 53
<212> TYPE: PRT
<213> ORGANISM: Artificial sequence
<220> FEATURE:
<223> OTHER INFORMATION: Synthetic peptide

<400> SEQUENCE: 7

His His His His His His Ser Ile Arg Lys Leu Glu Tyr Glu Ile Glu
1               5                   10                  15

Glu Leu Arg Leu Arg Ile Gly Gly Thr Phe Val Glu Thr Gly Ser
            20                  25                  30

Gly Thr Ser Lys Gln Val Ala Lys Arg Val Ala Ala Glu Lys Leu Leu
        35                  40                  45

Thr Lys Phe Lys Thr
    50

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

His His His His His His
1               5

<210> SEQ ID NO 9
<211> LENGTH: 58
<212> TYPE: PRT
<213> ORGANISM: Artificial sequence
<220> FEATURE:
<223> OTHER INFORMATION: Synthetic peptide

<400> SEQUENCE: 9

Cys Arg Gly Asp Cys His His His His His Ser Ile Arg Lys Leu
1               5                   10                  15

Glu Tyr Glu Ile Glu Glu Leu Arg Leu Arg Ile Gly Gly Thr Phe
            20                  25                  30

Val Glu Thr Gly Ser Gly Thr Ser Lys Gln Val Ala Lys Arg Val Ala
        35                  40                  45

Ala Glu Lys Leu Leu Thr Lys Phe Lys Thr
        50                  55

<210> SEQ ID NO 10
<211> LENGTH: 11
<212> TYPE: PRT
<213> ORGANISM: Artificial sequence
<220> FEATURE:
<223> OTHER INFORMATION: Synthetic peptide

<400> SEQUENCE: 10

Cys Arg Gly Asp Cys His His His His His His
1               5                   10
```

<210> SEQ ID NO 11
<211> LENGTH: 46
<212> TYPE: PRT
<213> ORGANISM: Artificial sequence
<220> FEATURE:
<223> OTHER INFORMATION: Synthetic peptide

<400> SEQUENCE: 11

```
Ala Met Leu Lys Ala Met Leu Lys Ala Met Ala Glu Leu Met Ala Lys
1               5                   10                  15

Leu Tyr Thr Phe Val Glu Thr Gly Ser Gly Thr Ser Lys Gln Val Ala
            20                  25                  30

Lys Arg Val Ala Ala Glu Lys Leu Leu Thr Lys Phe Lys Thr
        35                  40                  45
```

<210> SEQ ID NO 12
<211> LENGTH: 18
<212> TYPE: PRT
<213> ORGANISM: Artificial sequence
<220> FEATURE:
<223> OTHER INFORMATION: Synthetic peptide

<400> SEQUENCE: 12

```
Ala Met Leu Lys Ala Met Leu Lys Ala Met Ala Glu Leu Met Ala Lys
1               5                   10                  15

Leu Tyr
```

<210> SEQ ID NO 13
<211> LENGTH: 14
<212> TYPE: PRT
<213> ORGANISM: Artificial sequence
<220> FEATURE:
<223> OTHER INFORMATION: Synthetic peptide

<400> SEQUENCE: 13

```
Gly Gly Pro Lys Lys Lys Arg Lys Val Glu Asp Pro Thr Gly
1               5                   10
```

<210> SEQ ID NO 14
<211> LENGTH: 14
<212> TYPE: PRT
<213> ORGANISM: Artificial sequence
<220> FEATURE:
<223> OTHER INFORMATION: Synthetic peptide

<400> SEQUENCE: 14

```
Gly Gly Pro Lys Thr Lys Arg Lys Val Glu Asp Pro Thr Gly
1               5                   10
```

<210> SEQ ID NO 15
<211> LENGTH: 13
<212> TYPE: PRT
<213> ORGANISM: Artificial sequence
<220> FEATURE:
<223> OTHER INFORMATION: Synthetic peptide

<400> SEQUENCE: 15

```
Gly Gly Gly Gly Gly Gly Pro Lys Lys Arg Lys Val Gly
1               5                   10
```

<210> SEQ ID NO 16
<211> LENGTH: 13
<212> TYPE: PRT
<213> ORGANISM: Artificial sequence
<220> FEATURE:

<223> OTHER INFORMATION: Synthetic peptide

<400> SEQUENCE: 16

Lys Lys Lys Lys Lys Lys Pro Lys Lys Arg Lys Val Gly
1               5                   10

<210> SEQ ID NO 17
<211> LENGTH: 39
<212> TYPE: PRT
<213> ORGANISM: Artificial sequence
<220> FEATURE:
<223> OTHER INFORMATION: Synthetic peptide

<400> SEQUENCE: 17

Gly Gly Asn Gln Ser Ser Asn Phe Gly Pro Met Lys Gly Gly Asn Phe
1               5                   10                  15

Gly Gly Arg Ser Ser Gly Pro Tyr Gly Gly Gly Gln Tyr Phe Ala Lys
                20                  25                  30

Pro Arg Asn Gln Gly Gly Tyr
            35

<210> SEQ ID NO 18
<211> LENGTH: 11
<212> TYPE: PRT
<213> ORGANISM: Artificial sequence
<220> FEATURE:
<223> OTHER INFORMATION: Synthetic peptide

<400> SEQUENCE: 18

Gly Gly Pro Ala Ala Lys Arg Val Lys Leu Asp
1               5                   10

<210> SEQ ID NO 19
<211> LENGTH: 17
<212> TYPE: PRT
<213> ORGANISM: Artificial sequence
<220> FEATURE:
<223> OTHER INFORMATION: Synthetic peptide

<400> SEQUENCE: 19

Gly Gly Lys Arg Ala Ala Thr Lys Lys Ala Gly Gln Ala Lys Lys Lys
1               5                   10                  15

Lys

<210> SEQ ID NO 20
<211> LENGTH: 26
<212> TYPE: PRT
<213> ORGANISM: Artificial sequence
<220> FEATURE:
<223> OTHER INFORMATION: Synthetic peptide

<400> SEQUENCE: 20

Gly Gly Val Arg Lys Lys Arg Lys Thr Glu Glu Glu Ser Pro Leu Lys
1               5                   10                  15

Asp Lys Asp Ala Lys Lys Ser Lys Gln Glu
            20                  25

<210> SEQ ID NO 21
<211> LENGTH: 26
<212> TYPE: PRT
<213> ORGANISM: Artificial sequence
<220> FEATURE:
<223> OTHER INFORMATION: Synthetic peptide

<400> SEQUENCE: 21

Gly Gly Arg Leu Arg Arg Asp Ala Gly Gly Arg Gly Val Tyr Gln
1               5                   10                  15

His Leu Gly Gly Ala Pro Arg Arg Lys
            20                  25

<210> SEQ ID NO 22
<211> LENGTH: 21
<212> TYPE: PRT
<213> ORGANISM: Artificial sequence
<220> FEATURE:
<223> OTHER INFORMATION: Synthetic peptide

<400> SEQUENCE: 22

Gly Gly Lys Arg Lys Gly Asp Glu Val Asp Gly Val Asp Gln Cys Ala
1               5                   10                  15

Lys Lys Ser Lys Lys
            20

<210> SEQ ID NO 23
<211> LENGTH: 27
<212> TYPE: PRT
<213> ORGANISM: Artificial sequence
<220> FEATURE:
<223> OTHER INFORMATION: Synthetic peptide

<400> SEQUENCE: 23

Gly Gly Ile Gly Ala Val Leu Lys Val Leu Thr Thr Gly Leu Pro Ala
1               5                   10                  15

Leu Ile Ser Trp Ile Lys Arg Lys Arg Gln Gln
            20                  25

<210> SEQ ID NO 24
<211> LENGTH: 27
<212> TYPE: PRT
<213> ORGANISM: Artificial sequence
<220> FEATURE:
<223> OTHER INFORMATION: Synthetic peptide

<400> SEQUENCE: 24

Gly Gly Ile Gly Ala Val Leu Lys Val Leu Thr Thr Gly Leu Pro Ala
1               5                   10                  15

Leu Ile Ser Trp Ile Lys Arg Lys Arg Glu Glu
            20                  25

<210> SEQ ID NO 25
<211> LENGTH: 24
<212> TYPE: PRT
<213> ORGANISM: Artificial sequence
<220> FEATURE:
<223> OTHER INFORMATION: Synthetic peptide

<400> SEQUENCE: 25

Gly Gly Leu Phe Glu Ala Ile Ala Gly Phe Ile Glu Asn Gly Trp Glu
1               5                   10                  15

Gly Met Ile Asn Gly Trp Tyr Gly
            20

<210> SEQ ID NO 26
<211> LENGTH: 25
<212> TYPE: PRT
<213> ORGANISM: Artificial sequence
<220> FEATURE:
<223> OTHER INFORMATION: Synthetic peptide

```
<400> SEQUENCE: 26

Gly Gly Leu Phe His Ala Ile Ala Ala His Phe Ile His Gly Gly Trp
1               5                   10                  15

His Gly Leu Ile His Gly Trp Trp Gly
            20                  25

<210> SEQ ID NO 27
<211> LENGTH: 36
<212> TYPE: PRT
<213> ORGANISM: Artificial sequence
<220> FEATURE:
<223> OTHER INFORMATION: Synthetic peptide

<400> SEQUENCE: 27

Gly Gly Trp Glu Ala Ala Leu Ala Glu Ala Leu Ala Glu Ala Leu Ala
1               5                   10                  15

Glu His Leu Ala Glu Ala Leu Ala Leu Glu Ala Leu Glu Ala Leu Glu
            20                  25                  30

Ala Leu Ala Ala
            35

<210> SEQ ID NO 28
<211> LENGTH: 33
<212> TYPE: PRT
<213> ORGANISM: Artificial sequence
<220> FEATURE:
<223> OTHER INFORMATION: Synthetic peptide

<400> SEQUENCE: 28

Gly Gly Trp Glu Ala Lys Leu Ala Lys Ala Leu Ala Lys Ala Leu Ala
1               5                   10                  15

Lys His Leu Ala Lys Ala Leu Ala Lys Ala Leu Ala Lys Ala Leu Ala
            20                  25                  30

Ala

<210> SEQ ID NO 29
<211> LENGTH: 21
<212> TYPE: PRT
<213> ORGANISM: Artificial sequence
<220> FEATURE:
<223> OTHER INFORMATION: Synthetic peptide

<400> SEQUENCE: 29

Gly Gly Leu Phe Glu Ala Leu Leu Glu Leu Leu Glu Ser Leu Trp Glu
1               5                   10                  15

Leu Leu Leu Glu Ala
            20

<210> SEQ ID NO 30
<211> LENGTH: 21
<212> TYPE: PRT
<213> ORGANISM: Artificial sequence
<220> FEATURE:
<223> OTHER INFORMATION: Synthetic peptide

<400> SEQUENCE: 30

Gly Gly Leu Phe Lys Ala Leu Leu Lys Leu Leu Lys Ser Leu Trp Lys
1               5                   10                  15

Leu Leu Leu Lys Ala
            20

<210> SEQ ID NO 31
```

```
<211> LENGTH: 25
<212> TYPE: PRT
<213> ORGANISM: Artificial sequence
<220> FEATURE:
<223> OTHER INFORMATION: Synthetic peptide

<400> SEQUENCE: 31

Gly Gly Lys Phe Thr Ile Val Phe Pro His Asn Gln Lys Gly Asn Trp
1               5                   10                  15

Lys Asn Val Pro Ser Asn Tyr His Tyr
            20                  25

<210> SEQ ID NO 32
<211> LENGTH: 18
<212> TYPE: PRT
<213> ORGANISM: Artificial sequence
<220> FEATURE:
<223> OTHER INFORMATION: Synthetic peptide

<400> SEQUENCE: 32

Gly Gly Arg Glu Ile Lys Ile Trp Phe Glu Asn Arg Arg Met Lys Trp
1               5                   10                  15

Lys Lys

<210> SEQ ID NO 33
<211> LENGTH: 28
<212> TYPE: PRT
<213> ORGANISM: Artificial sequence
<220> FEATURE:
<223> OTHER INFORMATION: Synthetic peptide

<400> SEQUENCE: 33

Gly Gly Trp Thr Leu Asn Ser Ala Gly Tyr Leu Leu Gly Lys Ile Asn
1               5                   10                  15

Leu Lys Ala Leu Ala Ala Leu Ala Lys Lys Ile Leu
            20                  25

<210> SEQ ID NO 34
<211> LENGTH: 9
<212> TYPE: PRT
<213> ORGANISM: Artificial sequence
<220> FEATURE:
<223> OTHER INFORMATION: Synthetic peptide

<400> SEQUENCE: 34

Cys Asp Cys Arg Gly Asp Cys Phe Cys
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic peptide

<400> SEQUENCE: 35

Cys Asn Gly Arg Cys
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic peptide
```

```
<400> SEQUENCE: 36

Cys Pro Arg Glu Cys Glu Ser Ile Cys
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic peptide

<400> SEQUENCE: 37

Cys Pro Gly Pro Glu Gly Ala Gly Cys
1               5

<210> SEQ ID NO 38
<211> LENGTH: 10
<212> TYPE: PRT
<213> ORGANISM: Artificial sequence
<220> FEATURE:
<223> OTHER INFORMATION: Synthetic peptide

<400> SEQUENCE: 38

Cys Thr Thr His Trp Gly Phe Thr Leu Cys
1               5                   10

<210> SEQ ID NO 39
<211> LENGTH: 10
<212> TYPE: PRT
<213> ORGANISM: Artificial sequence
<220> FEATURE:
<223> OTHER INFORMATION: Synthetic peptide

<400> SEQUENCE: 39

Cys Arg Arg His Trp Gly Phe Glu Phe Cys
1               5                   10

<210> SEQ ID NO 40
<211> LENGTH: 3
<212> TYPE: PRT
<213> ORGANISM: Artificial sequence
<220> FEATURE:
<223> OTHER INFORMATION: Synthetic peptide

<400> SEQUENCE: 40

Gly Leu Ser
1

<210> SEQ ID NO 41
<211> LENGTH: 9
<212> TYPE: PRT
<213> ORGANISM: Artificial sequence
<220> FEATURE:
<223> OTHER INFORMATION: Synthetic peptide

<400> SEQUENCE: 41

Cys Gly Arg Arg Ala Gly Gly Ser Cys
1               5

<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42
```

Cys Val Pro Glu Leu Gly His Glu Cys
1               5

<210> SEQ ID NO 43
<211> LENGTH: 12
<212> TYPE: PRT
<213> ORGANISM: Artificial sequence
<220> FEATURE:
<223> OTHER INFORMATION: Synthetic peptide

<400> SEQUENCE: 43

His Thr Met Tyr Tyr His His Tyr Gln His His Leu
1               5                   10

<210> SEQ ID NO 44
<211> LENGTH: 7
<212> TYPE: PRT
<213> ORGANISM: Artificial sequence
<220> FEATURE:
<223> OTHER INFORMATION: Synthetic peptide

<400> SEQUENCE: 44

Val His Ser Pro Asn Lys Lys
1               5

<210> SEQ ID NO 45
<211> LENGTH: 9
<212> TYPE: PRT
<213> ORGANISM: Artificial sequence
<220> FEATURE:
<223> OTHER INFORMATION: Synthetic peptide

<400> SEQUENCE: 45

Cys Ser Arg Pro Arg Arg Ser Glu Cys
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic peptide

<400> SEQUENCE: 46

Cys Arg Gly Arg Arg Ser Thr
1               5

<210> SEQ ID NO 47
<211> LENGTH: 15
<212> TYPE: PRT
<213> ORGANISM: Artificial sequence
<220> FEATURE:
<223> OTHER INFORMATION: Synthetic peptide

<400> SEQUENCE: 47

Ile Cys Arg Arg Ala Arg Gly Asp Asn Pro Asp Asp Arg Cys Thr
1               5                   10                  15

<210> SEQ ID NO 48
<211> LENGTH: 12
<212> TYPE: PRT
<213> ORGANISM: Artificial sequence
<220> FEATURE:
<223> OTHER INFORMATION: Synthetic peptide

<400> SEQUENCE: 48

```
Pro Leu Ala Glu Ile Asp Gly Ile Glu Leu Thr Tyr
1               5                   10

<210> SEQ ID NO 49
<211> LENGTH: 27
<212> TYPE: PRT
<213> ORGANISM: Artificial sequence
<220> FEATURE:
<223> OTHER INFORMATION: Synthetic peptide

<400> SEQUENCE: 49

His Ser Asp Gly Thr Phe Thr Ser Glu Leu Ser Arg Leu Arg Asp Ser
1               5                   10                  15

Ala Arg Leu Gln Arg Leu Leu Gln Gly Leu Val
            20                  25

<210> SEQ ID NO 50
<211> LENGTH: 16
<212> TYPE: PRT
<213> ORGANISM: Artificial sequence
<220> FEATURE:
<223> OTHER INFORMATION: Synthetic peptide

<400> SEQUENCE: 50

Asn Pro Val Val Gly Tyr Ile Gly Glu Arg Pro Gln Tyr Arg Asp Leu
1               5                   10                  15

<210> SEQ ID NO 51
<211> LENGTH: 29
<212> TYPE: PRT
<213> ORGANISM: Artificial sequence
<220> FEATURE:
<223> OTHER INFORMATION: Synthetic peptide

<400> SEQUENCE: 51

Cys Thr Thr Thr His Thr Phe Val Lys Ala Leu Thr Met Asp Gly Lys
1               5                   10                  15

Gln Ala Ala Trp Arg Phe Ile Arg Ile Asp Thr Ala Cys
            20                  25

<210> SEQ ID NO 52
<211> LENGTH: 14
<212> TYPE: PRT
<213> ORGANISM: Artificial sequence
<220> FEATURE:
<223> OTHER INFORMATION: Synthetic peptide

<400> SEQUENCE: 52

Glu Leu Tyr Glu Asn Lys Ile Pro Arg Arg Pro Tyr Ile Leu
1               5                   10

<210> SEQ ID NO 53
<211> LENGTH: 7
<212> TYPE: PRT
<213> ORGANISM: Artificial sequence
<220> FEATURE:
<223> OTHER INFORMATION: Synthetic peptide

<400> SEQUENCE: 53

Leu Ser Ile Pro Pro Lys Ala
1               5

<210> SEQ ID NO 54
<211> LENGTH: 7
<212> TYPE: PRT
<213> ORGANISM: Artificial sequence
```

```
<220> FEATURE:
<223> OTHER INFORMATION: Synthetic peptide

<400> SEQUENCE: 54

Phe Gln Thr Pro Pro Gln Leu
1               5

<210> SEQ ID NO 55
<211> LENGTH: 7
<212> TYPE: PRT
<213> ORGANISM: Artificial sequence
<220> FEATURE:
<223> OTHER INFORMATION: Synthetic peptide

<400> SEQUENCE: 55

Leu Thr Pro Ala Thr Ala Ile
1               5

<210> SEQ ID NO 56
<211> LENGTH: 9
<212> TYPE: PRT
<213> ORGANISM: Artificial sequence
<220> FEATURE:
<223> OTHER INFORMATION: Synthetic peptide

<400> SEQUENCE: 56

Cys Tyr Ile Gln Asn Cys Pro Leu Gly
1               5

<210> SEQ ID NO 57
<211> LENGTH: 9
<212> TYPE: PRT
<213> ORGANISM: Artificial sequence
<220> FEATURE:
<223> OTHER INFORMATION: Synthetic peptide

<400> SEQUENCE: 57

Val Tyr Phe Gln Asn Cys Pro Arg Gly
1               5

<210> SEQ ID NO 58
<211> LENGTH: 13
<212> TYPE: PRT
<213> ORGANISM: Artificial sequence
<220> FEATURE:
<223> OTHER INFORMATION: Synthetic peptide

<400> SEQUENCE: 58

Ser Tyr Ser Met Glu His Phe Arg Trp Gly Lys Pro Val
1               5                   10

<210> SEQ ID NO 59
<211> LENGTH: 22
<212> TYPE: PRT
<213> ORGANISM: Artificial sequence
<220> FEATURE:
<223> OTHER INFORMATION: Synthetic peptide

<400> SEQUENCE: 59

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 60
<211> LENGTH: 12
```

<212> TYPE: PRT
<213> ORGANISM: Artificial sequence
<220> FEATURE:
<223> OTHER INFORMATION: Synthetic peptide

<400> SEQUENCE: 60

Tyr Val Met Gly His Phe Arg Trp Asp Arg Phe Gly
1               5                   10

<210> SEQ ID NO 61
<211> LENGTH: 39
<212> TYPE: PRT
<213> ORGANISM: Artificial sequence
<220> FEATURE:
<223> OTHER INFORMATION: Synthetic peptide

<400> SEQUENCE: 61

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 62
<211> LENGTH: 41
<212> TYPE: PRT
<213> ORGANISM: Artificial sequence
<220> FEATURE:
<223> OTHER INFORMATION: Synthetic peptide

<400> SEQUENCE: 62

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 63
<211> LENGTH: 10
<212> TYPE: PRT
<213> ORGANISM: Artificial sequence
<220> FEATURE:
<223> OTHER INFORMATION: Synthetic peptide

<400> SEQUENCE: 63

Glu His Trp Ser Tyr Gly Leu Arg Pro Gly
1               5                   10

<210> SEQ ID NO 64
<211> LENGTH: 3
<212> TYPE: PRT
<213> ORGANISM: Artificial sequence
<220> FEATURE:
<223> OTHER INFORMATION: Synthetic peptide

<400> SEQUENCE: 64

Glu His Pro
1

<210> SEQ ID NO 65
<211> LENGTH: 14
<212> TYPE: PRT
<213> ORGANISM: Artificial sequence

```
<220> FEATURE:
<223> OTHER INFORMATION: Synthetic peptide

<400> SEQUENCE: 65

Ala Gly Cys Lys Asn Phe Phe Trp Lys Thr Phe Thr Ser Cys
1               5                   10

<210> SEQ ID NO 66
<211> LENGTH: 32
<212> TYPE: PRT
<213> ORGANISM: Artificial sequence
<220> FEATURE:
<223> OTHER INFORMATION: Synthetic peptide

<400> SEQUENCE: 66

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 67
<211> LENGTH: 31
<212> TYPE: PRT
<213> ORGANISM: Artificial sequence
<220> FEATURE:
<223> OTHER INFORMATION: Synthetic peptide

<400> SEQUENCE: 67

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 68
<211> LENGTH: 28
<212> TYPE: PRT
<213> ORGANISM: Artificial sequence
<220> FEATURE:
<223> OTHER INFORMATION: Synthetic peptide

<400> SEQUENCE: 68

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 69
<211> LENGTH: 23
<212> TYPE: PRT
<213> ORGANISM: Artificial sequence
<220> FEATURE:
<223> OTHER INFORMATION: Synthetic peptide

<400> SEQUENCE: 69

Phe Asn Ala Pro Phe Asp Val Gly Ile Lys Leu Ser Gly Val Gln Tyr
1               5                   10                  15

Gln Gln His Ser Gln Ala Leu
            20

<210> SEQ ID NO 70
<211> LENGTH: 17
<212> TYPE: PRT
<213> ORGANISM: Artificial sequence
<220> FEATURE:
<223> OTHER INFORMATION: Synthetic peptide
```

<400> SEQUENCE: 70

Pro Gly Pro Trp Leu Glu Glu Glu Glu Ala Tyr Gly Trp Met Asp
1               5                   10                  15

Phe

<210> SEQ ID NO 71
<211> LENGTH: 27
<212> TYPE: PRT
<213> ORGANISM: Artificial sequence
<220> FEATURE:
<223> OTHER INFORMATION: Synthetic peptide

<400> SEQUENCE: 71

His Ser Asp Gly Thr Phe Thr Ser Glu Leu Ser Arg Leu Asn Asp Ser
1               5                   10                  15

Ala Arg Leu Asn Arg Leu Leu Asn Gly Leu Val
            20                  25

<210> SEQ ID NO 72
<211> LENGTH: 21
<212> TYPE: PRT
<213> ORGANISM: Artificial sequence
<220> FEATURE:
<223> OTHER INFORMATION: Synthetic peptide

<400> SEQUENCE: 72

Lys Ala Pro Ser Gly Arg Val Ser Met Ile Lys Asn Leu Gln Ser Leu
1               5                   10                  15

Asp Pro Ser His Arg
            20

<210> SEQ ID NO 73
<211> LENGTH: 28
<212> TYPE: PRT
<213> ORGANISM: Artificial sequence
<220> FEATURE:
<223> OTHER INFORMATION: Synthetic peptide

<400> SEQUENCE: 73

His Ser Asp Ala Val Phe Thr Asp Asn Tyr Thr Arg Leu Arg Lys Gly
1               5                   10                  15

Met Ala Val Lys Lys Tyr Leu Asn Ser Ile Leu Asn
            20                  25

<210> SEQ ID NO 74
<211> LENGTH: 11
<212> TYPE: PRT
<213> ORGANISM: Artificial sequence
<220> FEATURE:
<223> OTHER INFORMATION: Synthetic peptide

<400> SEQUENCE: 74

Arg Pro Lys Pro Gln Gln Phe Phe Gly Leu Met
1               5                   10

<210> SEQ ID NO 75
<211> LENGTH: 36
<212> TYPE: PRT
<213> ORGANISM: Artificial sequence
<220> FEATURE:
<223> OTHER INFORMATION: Synthetic peptide

<400> SEQUENCE: 75

Ala Pro Leu Glu Pro Val Tyr Pro Gly Asp Asn Ala Thr Pro Glu Asn
1               5                   10                  15

Met Ala Gln Tyr Ala Ala Asp Leu Arg Arg Tyr Ile Asn Met Leu Thr
            20                  25                  30

Arg Pro Arg Tyr
            35

<210> SEQ ID NO 76
<211> LENGTH: 36
<212> TYPE: PRT
<213> ORGANISM: Artificial sequence
<220> FEATURE:
<223> OTHER INFORMATION: Synthetic peptide

<400> SEQUENCE: 76

Tyr Pro Pro Lys Pro Glu Ser Pro Gly Glu Asp Ala Ser Pro Glu Glu
1               5                   10                  15

Met Asn Lys Tyr Leu Thr Ala Leu Arg His Tyr Ile Asn Leu Val Thr
            20                  25                  30

Arg Gln Arg Tyr
            35

<210> SEQ ID NO 77
<211> LENGTH: 36
<212> TYPE: PRT
<213> ORGANISM: Artificial sequence
<220> FEATURE:
<223> OTHER INFORMATION: Synthetic peptide

<400> SEQUENCE: 77

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 78
<211> LENGTH: 29
<212> TYPE: PRT
<213> ORGANISM: Artificial sequence
<220> FEATURE:
<223> OTHER INFORMATION: Synthetic peptide

<400> SEQUENCE: 78

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 79
<211> LENGTH: 8
<212> TYPE: PRT
<213> ORGANISM: Artificial sequence
<220> FEATURE:
<223> OTHER INFORMATION: Synthetic peptide

<400> SEQUENCE: 79

Asp Arg Val Tyr Ile His Pro Phe
1               5

<210> SEQ ID NO 80
<211> LENGTH: 40

<212> TYPE: PRT
<213> ORGANISM: Artificial sequence
<220> FEATURE:
<223> OTHER INFORMATION: Synthetic peptide

<400> SEQUENCE: 80

Phe Val Pro Tyr Asn Pro Pro Arg Pro Gly Gln Ser Lys Pro Phe Pro
1               5                   10                  15

Ser Phe Pro Gly His Gly Pro Phe Asn Pro Lys Ile Gln Trp Pro Tyr
            20                  25                  30

Pro Leu Pro Asn Pro Pro Gly His
            35                  40

<210> SEQ ID NO 81
<211> LENGTH: 17
<212> TYPE: PRT
<213> ORGANISM: Artificial sequence
<220> FEATURE:
<223> OTHER INFORMATION: Synthetic peptide

<400> SEQUENCE: 81

Gly Asn Arg Pro Val Tyr Ile Pro Pro Pro Arg Pro Pro His Pro Arg
1               5                   10                  15

Leu

<210> SEQ ID NO 82
<211> LENGTH: 46
<212> TYPE: PRT
<213> ORGANISM: Artificial sequence
<220> FEATURE:
<223> OTHER INFORMATION: Synthetic peptide

<400> SEQUENCE: 82

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

Pro Pro Phe Arg Pro Pro Leu Gly Pro Phe Pro Gly Arg Arg
            35                  40                  45

<210> SEQ ID NO 83
<211> LENGTH: 66
<212> TYPE: PRT
<213> ORGANISM: Artificial sequence
<220> FEATURE:
<223> OTHER INFORMATION: Synthetic peptide

<400> SEQUENCE: 83

Ala Leu Ser Tyr Arg Glu Ala Val Leu Arg Ala Val Asp Arg Ile Asn
1               5                   10                  15

Glu Arg Ser Ser Glu Ala Asn Leu Tyr Arg Leu Leu Glu Leu Asp Pro
            20                  25                  30

Pro Pro Lys Asp Val Glu Asp Arg Gly Ala Arg Lys Pro Thr Ser Phe
            35                  40                  45

Thr Val Lys Glu Thr Val Pro Arg Thr Ser Pro Gln Pro Pro Glu Gln
    50                  55                  60

Cys Asp
65

<210> SEQ ID NO 84
<211> LENGTH: 64
<212> TYPE: PRT

<213> ORGANISM: Artificial sequence
<220> FEATURE:
<223> OTHER INFORMATION: Synthetic peptide

<400> SEQUENCE: 84

```
Met Lys Phe Thr Ile Val Phe Leu Leu Leu Ala Cys Val Phe Ala Met
1               5                   10                  15

Ala Val Ala Thr Pro Gly Lys Pro Arg Pro Tyr Ser Pro Arg Pro Thr
            20                  25                  30

Ser His Pro Arg Pro Ile Arg Val Arg Arg Glu Ala Leu Ala Ile Glu
        35                  40                  45

Asp His Leu Ala Gln Ala Ala Ile Arg Pro Pro Ile Leu Pro Ala
    50                  55                  60
```

<210> SEQ ID NO 85
<211> LENGTH: 79
<212> TYPE: PRT
<213> ORGANISM: Artificial sequence
<220> FEATURE:
<223> OTHER INFORMATION: Synthetic peptide

<400> SEQUENCE: 85

```
Ala Phe Pro Pro Pro Asn Val Pro Gly Pro Arg Phe Pro Pro Pro Asn
1               5                   10                  15

Phe Pro Gly Pro Arg Phe Pro Pro Pro Asn Phe Pro Gly Pro Arg Phe
            20                  25                  30

Pro Pro Pro Asn Phe Pro Gly Pro Arg Phe Pro Pro Pro Asn Phe Pro
        35                  40                  45

Gly Pro Pro Phe Pro Pro Pro Ile Phe Pro Gly Pro Trp Phe Pro Pro
    50                  55                  60

Pro Pro Pro Phe Arg Pro Pro Pro Phe Gly Pro Pro Arg Phe Pro
65                  70                  75
```

<210> SEQ ID NO 86
<211> LENGTH: 28
<212> TYPE: PRT
<213> ORGANISM: Artificial sequence
<220> FEATURE:
<223> OTHER INFORMATION: Synthetic peptide

<400> SEQUENCE: 86

```
Cys Tyr Cys Arg Ile Pro Ala Cys Leu Ala Gly Glu Arg Arg Tyr Gly
1               5                   10                  15

Thr Cys Phe Leu Gly Arg Val Trp Ala Phe Cys Cys
            20                  25
```

<210> SEQ ID NO 87
<211> LENGTH: 36
<212> TYPE: PRT
<213> ORGANISM: Artificial sequence
<220> FEATURE:
<223> OTHER INFORMATION: Synthetic peptide

<400> SEQUENCE: 87

```
Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35
```

```
<210> SEQ ID NO 88
<211> LENGTH: 18
<212> TYPE: PRT
<213> ORGANISM: Artificial sequence
<220> FEATURE:
<223> OTHER INFORMATION: Synthetic peptide

<400> SEQUENCE: 88

Arg Gly Gly Arg Leu Cys Tyr Cys Arg Arg Phe Cys Val Cys Val
1               5                  10                  15

Gly Arg

<210> SEQ ID NO 89
<211> LENGTH: 44
<212> TYPE: PRT
<213> ORGANISM: Artificial sequence
<220> FEATURE:
<223> OTHER INFORMATION: Synthetic peptide

<400> SEQUENCE: 89

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
                20                  25                  30

Cys Ser Pro Ser Leu Lys Cys Trp Cys Glu Gly Cys
            35                  40

<210> SEQ ID NO 90
<211> LENGTH: 6
<212> TYPE: PRT
<213> ORGANISM: Artificial sequence
<220> FEATURE:
<223> OTHER INFORMATION: Synthetic peptide

<400> SEQUENCE: 90

Asp Glu Asp Met Asp Glu
1               5

<210> SEQ ID NO 91
<211> LENGTH: 34
<212> TYPE: PRT
<213> ORGANISM: Artificial sequence
<220> FEATURE:
<223> OTHER INFORMATION: Synthetic peptide

<400> SEQUENCE: 91

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
                20                  25                  30

Thr Gln

<210> SEQ ID NO 92
<211> LENGTH: 24
<212> TYPE: PRT
<213> ORGANISM: Artificial sequence
<220> FEATURE:
<223> OTHER INFORMATION: Synthetic peptide

<400> SEQUENCE: 92

Gly Ile Gly Ala Leu Ser Ala Lys Gly Ala Leu Lys Gly Leu Ala Lys
1               5                   10                  15

Gly Leu Ala Glx His Phe Ala Asn
                20
```

```
<210> SEQ ID NO 93
<211> LENGTH: 32
<212> TYPE: PRT
<213> ORGANISM: Artificial sequence
<220> FEATURE:
<223> OTHER INFORMATION: Synthetic peptide

<400> SEQUENCE: 93

Trp Lys Pro Phe Lys Lys Ile Glu Lys Ala Val Arg Arg Val Arg Asp
1               5                   10                  15

Gly Val Ala Lys Ala Gly Pro Ala Val Ala Val Val Gly Gln Ala Thr
            20                  25                  30

<210> SEQ ID NO 94
<211> LENGTH: 46
<212> TYPE: PRT
<213> ORGANISM: Artificial sequence
<220> FEATURE:
<223> OTHER INFORMATION: Synthetic peptide

<400> SEQUENCE: 94

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Asp Ile Ala Gly Cys Lys Ile Lys Gly Glu Cys
        35                  40                  45

<210> SEQ ID NO 95
<211> LENGTH: 15
<212> TYPE: PRT
<213> ORGANISM: Artificial sequence
<220> FEATURE:
<223> OTHER INFORMATION: Synthetic peptide

<400> SEQUENCE: 95

Arg Ser Arg Arg Arg Arg Arg Arg Ser Cys Gln Thr Arg Arg Arg
1               5                   10                  15
```